United States Patent [19]

Vetter et al.

[11] Patent Number: 5,453,372
[45] Date of Patent: Sep. 26, 1995

[54] STABILIZED ENZYMES AND PROCESS FOR PREPARING THEM

[75] Inventors: Roman Vetter, Burgdorf; Ingo Muecke, Barsinghausen; Detlef Wilke, Wennigsen, all of Germany; Amory Antoine, Rixensart, Belgium; Wolfgang Aehle, Delft, Netherlands; Harald Sobek, Ummendorf; Dietmar Schomburg, Braunschwig, both of Germany; André Clippe, Walhain, Belgium

[73] Assignees: Solvay Enzymes GmbH & Co. KG, Nienburg/Weser; Gesellschaft fuer Bio-technologische Forschung, Braunschweig, both of Germany

[21] Appl. No.: 918,318

[22] Filed: Jul. 27, 1992

[30] Foreign Application Priority Data

Jul. 27, 1991 [DE] Germany .................. 41 24 997.6

[51] Int. Cl.[6] .................. C12N 9/50; C12N 9/54; C12N 9/56
[52] U.S. Cl. .................. 435/222; 435/221; 435/219
[58] Field of Search .................. 435/219, 221, 435/222

[56] References Cited

U.S. PATENT DOCUMENTS

| | | | |
|---|---|---|---|
| 3,770,587 | 11/1973 | Hamsher et al. | 435/188 |
| 4,760,025 | 7/1988 | Estell et al. | 435/222 |
| 4,914,031 | 4/1990 | Zukowski et al. | 435/222 |
| 4,990,452 | 2/1991 | Bryan et al. | 435/222 |

FOREIGN PATENT DOCUMENTS

| | | |
|---|---|---|
| 251446 | 1/1988 | European Pat. Off. . |
| 328229 | 8/1989 | European Pat. Off. . |
| 405901 | 1/1991 | European Pat. Off. . |
| 0405902 | 2/1991 | European Pat. Off. . |
| 415296 | 3/1991 | European Pat. Off. . |
| WO89/06279 | 1/1989 | WIPO . |
| 8906279 | 7/1989 | WIPO . |
| 91106637 | 5/1991 | WIPO . |

OTHER PUBLICATIONS

Van Der Laan, J. C., et al., Applied and Environmental Microbiology, vol. 57(4), pp. 901–909, Apr. 1991.
Wells, J. A., et al., Trends in Biochemical Sciences, vol. 13, pp. 291Δ297, Aug. 1988.
Bott, "Modeling and Crystallographic Analysis of Site–Specific Mutants of Subtilisin", *World Bio–Tech. Rep.* 2, 51–59 (1985).
Russell et al., "Rational Modification of Enzyme Catalysis by Engineering Surface Charge", *Nature*, 328:496–500 (1987).
Crossin, "Detergency and Biotechnology", *Soap/Cosmetics/Chemical Specialities*, 64 (4) 48–50 (1988).

*Primary Examiner*—Mindy B. Fleisher
*Attorney, Agent, or Firm*—Evenson, McKeown, Edwards & Lenahan

[57] ABSTRACT

Enzymes stabilized against the destabilizing effect of ionic surfactants and a method of producing such stabilized enzymes in which DNA sequences which code for the enzymes are modified by directed mutation in defined positions which correlate with defined surface regions of the enzyme, in such a way that the codon in which the mutation is located now codes for an amino acid differing from the original amino acid.

4 Claims, 21 Drawing Sheets

```
CTGGGAAGC  CGATTGCTA  CTGCATGTCG  TCGATTATTC  AAATGAACGC     50
CATCGCGAAA  TGGCAAAGAC  GACAAATGAA  ACACTCCAGG  CAATGGAAAT   100
CGATCGCCCG  ATGATTTATG  TTTACAACAA  AATGGATCAA  GTGAAAGACG   150
CGTTTCCTCA  AGCGCATGGC  ACGAGCTGTT  TATATCAGCT  AAGGCTAAAC   200
AAGGGCTTGA  TTTATTAGCA  CAGAAAATAG  CAAGCTATGT  TTTTCAAGAT   250
TTTGAAAAAC  ATCTGTTCAT  CATTCCTTAT  CGTGACGGGG  AGGCGGCTGC   300
TTATTTAAAC  AACCATGCCC  ATGTCCACAC  ACAGCGTGCT  GAGGAGGACG   350
GCTGGCATAT  CGTTGCCGAT  TTGCATGAAC  GAGACTTAAA  ACGGGTTGAA   400
AGCTACTGTG  TTTCAAAAGA  ACGATAATGA  AAAAAGCCAT  TTGAATGCTT   450
CTTGTTCAAA  TGGCTTTTTG  GCGACTATGG  TAGACAGATG  AACACTTGTT   500
TCGCTGTTTT  ACGACAAAGA  TCATCTTGCC  TGTTACGCGT  TTTTTAAATC   550
CGTTTTCGCA  CGTTCAATTG  TCGCCGAGTC  GTACCAGTCG  CTGTAAGTGA   600
GAATATGTTT  AGAAAGCCGC  GTATTTAAGC  GCAGTCTTTT  TCGTTCTGTA   650
CTGGCTGGTT  TGTGACAGTT  TCCATACCC  ATCAACCTCC  TTTTATTTGT    700
AGCTTTCCCC  ACTTGAAACC  GTTTAATCA  AAAACGAAGT  GAGAAGATTC    750
AGTTAACTTA  ACGTTAATAT  TTGTTTCCCA  ATAGGCAAAT  CTTTCTAACT   800
TTGATACGTT  TAAACTACCA  GCTTGGACAA  GTTGGTATAA  AATGAGGAG    850
GGAACCGA ATG AAG AAA CCG TTG GGG AAA ATT GTC GCA             888
         Met Lys Lys Pro Leu Gly Lys Ile Val Ala
         -110                 -105
```

FIG. 1

| | | | | | | | | | | | | |
|---|---|---|---|---|---|---|---|---|---|---|---|---|
| AGC | ACC | GCA | CTA | CTC | ATT | TCT | GTT | GCT | TTT | AGT | TCA | TCG |
| Ser | Thr | Ala | Leu | Leu | Ile | Ser | Val | Ala | Phe | Ser | Ser | Ser |
| -100 | | | | | -95 | | | | | | | -90 |
| ATC | GCA | TCG | GCT | GCT | GAA | GAA | GCA | AAA | GAA | AAA | TAT | TTA |
| Ile | Ala | Ser | Ala | Ala | Glu | Glu | Ala | Lys | Glu | Lys | Tyr | Leu |
| | | -85 | | | | | -80 | | | | | |
| ATT | GGC | TTT | AAT | GAG | CAG | GAA | GCT | GTC | AGT | GAG | TTT | GTA |
| Ile | Gly | Phe | Asn | Glu | Gln | Glu | Ala | Val | Ser | Glu | Phe | Val |
| -75 | | | | | -70 | | | | | -65 | | |
| GAA | CAA | GTA | GAG | GAA | AAT | GAC | GAG | GCA | ATT | CTC | TCT | |
| Glu | Gln | Val | Glu | Glu | Asn | Asp | Glu | Ala | Ile | Leu | Ser | |
| | -60 | | | | | -55 | | | | | -50 | |
| GAG | GAA | GAA | GTC | GAA | ATT | GAA | TTG | CTT | CAT | GAA | TTT | |
| Glu | Glu | Glu | Val | Glu | Ile | Glu | Leu | Leu | His | Glu | Phe | |
| | -45 | | | | | | | | -40 | | | |
| GAA | ACG | ATT | CCT | GTT | TTA | TCC | GTT | GAG | TTA | AGC | CCA | GAA |
| Glu | Thr | Ile | Pro | Val | Leu | Ser | Val | Glu | Leu | Ser | Pro | Glu |
| -35 | | | | | -30 | | | | | | | -25 |

```
GAT GTG GAC GCG CTT GAA CTC GAT CCA GCG ATT TCT TAT    1161
Asp Val Asp Ala Leu Glu Leu Asp Pro Ala Ile Ser Tyr
        -20                     -15

ATT GAA GAG GAT GCA GAA GTA ACG ACA ATG GCG CAA TCA    1200
Ile Glu Glu Asp Ala Glu Val Thr Thr Met Ala Gln Ser
        -10                      -5                1

GTG CCA TGG GGA ATT AGC CGT GTG CAA GCC CCA GCT GCC    1239
Val Pro Trp Gly Ile Ser Arg Val Gln Ala Pro Ala Ala
         5                      10                15

CAT AAC CGT GGA TTG ACA GGT TCT GGT GTA AAA GTT GCT    1278
His Asn Arg Gly Leu Thr Gly Ser Gly Val Lys Val Ala
        20                      25

GTC CTC GAT ACA GGT ATT TCC ACT CAT CCA GAC TTA AAT    1317
Val Leu Asp Thr Gly Ile Ser Thr His Pro Asp Leu Asn
        30                      35                40

ATT CGT GGT GGC GCT AGC TTT GTA CCA GGG GAA CCA TCC    1356
Ile Arg Gly Gly Ala Ser Phe Val Pro Gly Glu Pro Ser
        45                      50                55
```

FIG.1B

| | | | | | | | | | | | | | |
|---|---|---|---|---|---|---|---|---|---|---|---|---|---|
|ACT|CAA|GAT|GGG|AAT|GGG|CAT|ACG|CAT|GTG|GCC|GGG| |1395|
|Thr|Gln|Asp|Gly|Asn|Gly|His|Thr|His|Val|Ala|Gly| | |
| | | | |60| | |65| | | | | | |

ACG ATT GCT TTA AAC AAT TCG ATT GGC GTT CTT GGC  1434
Thr Ile Ala Leu Asn Asn Ser Ile Gly Val Leu Gly
 70              75              80

GTA GCG CCG AGC GCG GAA CTA TAC GCT GTT AAA TTA  1473
Val Ala Pro Ser Ala Glu Leu Tyr Ala Val Lys Val Leu
         85              90

GGG GCG AGC GGT TCA GGT TCG GTC AGC TCG ATT GCC CAA  1512
Gly Ala Ser Gly Ser Gly Ser Val Ser Ser Ile Ala Gln

GGA TTG GAA TGG GCA GGG AAC AAT GGC ATG CAC GTT GCT  1551
Gly Leu Glu Trp Ala Gly Asn Asn Gly Met His Val Ala
         110             115             120

AAT TTG AGT TTA GGA AGC CCT TCG CCA AGT GCC ACA CTT  1590
Asn Leu Ser Leu Gly Ser Pro Ser Pro Ser Ala Thr Leu
         125             130

FIG.1C

```
GAG CAA GCT GTT AAT AGC GCG ACT TCT AGA GGC GTT CTT        1629
Glu Gln Ala Val Asn Ser Ala Thr Ser Arg Gly Val Leu
135                 140                 145

GTT GTA GCG GCA TCT GGG AAT TCA GGT GCA GGC TCA ATC        1668
Val Val Ala Ala Ser Gly Asn Ser Gly Ala Gly Ser Ile
            150                 155

AGC TAT CCG GCC CGT TAT GCG AAC GCA ATG GCA GTC GGA        1707
Ser Tyr Pro Ala Arg Tyr Ala Asn Ala Met Ala Val Gly
160                 165                 170

GCT ACT GAC CAA AAC AAC CGC GCC AGC TTT TCA CAG            1746
Ala Thr Asp Gln Asn Asn Arg Ala Ser Phe Ser Gln
            175                 180             185

TAT GGC GCA GGG CTT GAC ATT GTC GCA CCA GGT GTA AAC        1785
Tyr Gly Ala Gly Leu Asp Ile Val Ala Pro Gly Val Asn
190                 195

GTG CAG AGC ACA TAC CCA GGT TCA ACG TAT GCC AGC TTA        1824
Val Gln Ser Thr Tyr Pro Gly Ser Thr Tyr Ala Ser Leu
200                 205                 210
```

FIG.1D

```
AAC GGT ACA TCG ATG GCT ACT CCT CAT GTT GCA GGT GCA    1863
Asn Gly Thr Ser Met Ala Thr Pro His Val Ala Gly Ala
            215                 220

GCA GCC CTT GTT AAA CAA AAG AAC CCA TCT TGG TCC AAT    1902
Ala Ala Leu Val Lys Gln Lys Asn Pro Ser Trp Ser Asn
225                 230                 235

GTA CAA ATC CGC AAT CAT CTA AAG AAT ACG GCA ACG AGC    1941
Val Gln Ile Arg Asn His Leu Lys Asn Thr Ala Thr Ser
            240                 245                 250

TTA GGA AGC ACG AAC TTG TAT GGA AGC GGA CTT GTC AAT    1980
Leu Gly Ser Thr Asn Leu Tyr Gly Ser Gly Leu Val Asn
                    255                 260

GCA GAA GCG GCA ACA CGC TAATCAATAA AAAAAGCCTG TGCGGTTAAA    2028
Ala Glu Ala Ala Thr Arg
265
```

FIG. 1E

```
GGGCACAGCG TTTTTTGTG TATGAATCGA AAAAGAGAAC AGATCGCAGG    2078
TCTCAAAAAT CGAGCGTAAA GGGCTGTTTA AAGCTCTTTA CGCTCGCAGG   2128
TCTTATCGCT ATACAATGGA AAATTCACGT CTTTTGACTT TCATGGCATA   2178
TTTATTTAAG TATTCGTTTG CTTTTTCGTA CTCTCCGTTT TTCTGGTACC   2228
ATTGCGCCAG CTCAATTGCA TAGTGGACTG GTTCTTCTTT ATTATCAAGC   2278
TT                                                       2280
```

FIG.1F (1)= Amino-acid sequence of the initial protease
(2)= DNA sequence of the initial protease
(3)= Oligonucleotide
(4)= New amino acid I.  Lys27--->Gln (K27Q)

```
                       27
(1):  Gly Ser Gly Val Lys Val Ala Val Leu Asp Thr Gly
(2):  GGT TCT GGT GTA AAA GTT GCT GTC CTC GAT ACA GG
                                  ScaI
(3):  GGT TCT GGT GTA cAA GTT GCa GTa CTC GAT ACA GG
(4):                  Gln
```

II.  Ile43--->Glu (I43E)

```
                               43
(1):  Ser Thr His Pro Asp Leu Asn Ile Arg Gly Gly Ala Ser
(2):   CC ACT CAT CCA GAC TTA AAT ATT CGT GGT GGC GCT AGC
                       Xho2
(3):   CC ACT CAT CCA GAt cTt AAT gaa CGT GGT GGC GCT AGC
(4):                               Glu
```

III.  Ile43--->Lys (I43K)

```
                           43
(1):  Thr His Pro Asp Leu Asn Ile Arg Gly Gly Ala
(2):  ACT CAT CCA GAC TTA AAT ATT CGT GGT GGC GCT
                       SwaI
(3):  ACT CAT CCA GAt TTA AAT aaa CGT GGT GGC GCT
(4):                           Lys
```

IV.  Ile43--->Gln (I43Q)

```
                       43
(1):  His Pro Asp Leu Asn Ile Arg Gly Gly Ala Ser
(2):  CAT CCA GAC TTA AAT ATT CGT GGT GGC GCT AGC
                       BstXI
(3):  CAT CCA GAC TTA AAc caa CGT GGT GGC GCT AGC
(4):                       Gln
```

FIG.3

V. Ile43--->Arg (I43R)

```
                         43
(1):   His Pro Asp Leu Asn Ile Arg Gly Gly Ala Ser
(2):   CAT CCA GAC TTA AAT ATT CGT GGT GGC GCT AGC
                             BglI
(3):   CAT CCA GAC TTA AAT cgc CGT GGT GGC GCT AGC
(4):                       Arg
```

VI. His118--->Trp (H118W)

```
                     118
(1):     Asn Gly Met His Val Ala Asn Leu Ser
(2):   C AAT GGC ATG CAC GTT GCT AAT TTG AGT TT
                         NruI
(3):   C AAT GGC ATG tgg GTc GCg AAT TTG AGT TT
(4):                 Trp
```

VII. His118--->Tyr (H118Y)

```
                         118
(1):     Gly Asn Asn Gly Met His Val Ala Asn Leu
(2):     GGG AAC AAT GGC ATG CAC GTT GCT AAT TTG
                             FokI
(3):     GGG AAC AAT GGg ATG tat GTT GCT AAT TTG
(4):                         Tyr
```

VIII. Arg143--->Asn (R143N)

```
                     143
(1):   Asn Ser Ala Thr Ser Arg Gly Val Leu
(2):   AAT AGC GCG ACT TCT AGA GGC GTT CTT
                         BatB1
(3):   AAT AGC GCG ACT TCg Aat GGC GTT CTT
(4):                   Asn
```

FIG. 3A

IX.  Arg143--->Ser (R143S)

```
                              143
(1):    Asn Ser Ala Thr Ser Arg Gly Val Leu
(2):    AAT AGC GCG ACT TCT AGA GGC GTT CTT
                       Tth111I
(3):    AAT AGC GCG ACT TCg tcg GGC GTT CTT
(4):                         Ser
```

X.  Arg143--->Thr (R143T)

```
                              143
(1):    Asn Ser Ala Thr Ser Arg Gly Val Leu
(2):    AAT AGC GCG ACT TCT AGA GGC GTT CTT
                         Sal1
(3):    AAT AGC GCG ACg TCg AcA GGC GTT CTT
(4):                         Thr
```

XI.  Arg164--->Gln (R164Q)

```
                              164
(1):    Ile Ser Tyr Pro Ala Arg Tyr Ala Asn Ala
(2):    ATC AGC TAT CCG GCC CGT TAT GCG AAC GCA
                         Fsp1
(3):    ATC AGC TAT CCt GCg Caa TAT GCG AAC GCA
(4):                         Gln
```

XII.  Asn237--->Pro (N237P)

```
                              237
(1):    Asn Pro Ser Trp Ser Asn Val Gln Ile Arg
(2):    AAC CCA TCT TGG TCC AAT GTA CAA ATC CGC
                       BstE2
(3):      C CCA TCT TGG TCa cca GTA CAA ATC CGC
(4):                         Pro
```

FIG. 3B

XIII. <u>Thr249--->Arg (T249R)</u>

```
                          249
(1):    Lys Asn Thr Ala Thr Ser Leu Gly Ser Thr
(2):    AAG AAT ACG GCA ACG AGC TTA GGA AGC ACG
                        Bsaa1
(3):    AAG AAT ACG GCA cgt AGC TTA GGA AGC ACG
(4):                    Arg
```

XIV. <u>Thr249--->Lys (T249K)</u>

```
                          249
(1):    Lys Asn Thr Ala Thr Ser Leu Gly Ser
(2):    AAG AAT ACG GCA ACG AGC TTA GGA AGC
                        Hind3
(3):    AAG AAT ACG GCA aaa AGC TTA GGA AGC
(4):                    Lys
```

XV. <u>Thr249--->Gln (T249Q)</u>

```
                          249
(1):    Lys Asn Thr Ala Thr Ser Leu Gly Ser
(2):    AAG AAT ACG GCA ACG AGC TTA GGA AGC
                        Hind3
(3):    AAG AAT ACG GCA caa AGC TTA GGA AGC
(4):                    Gln
```

XVI. <u>Thr 249--->Glu (T249E)</u>

```
                          249
(1):    Lys Asn Thr Ala Thr Ser Leu Gly Ser
(2):    AAG AAT ACG GCA ACG AGC TTA GGA AGC
                        Hind3
(3):    AAG AAT ACG GCA gaa AGC TTA GGA AGC
(4):                    Glu
```

FIG.3C

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 2280 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Bacillus alcalophilus
        ( B ) STRAIN: HA1, DSM 5466

( i x ) FEATURE:
        ( A ) NAME/KEY: CDS
        ( B ) LOCATION: 859..1998

( i x ) FEATURE:
        ( A ) NAME/KEY: mat_peptide
        ( B ) LOCATION: 1192..1998

( x i ) SEQUENCE DESCRIPTION: SEQ ID NO:1:

```
CTCGGGAAGC  CGATTTGCTA  CTGCATGTCG  TCGATTATTC  AAATGAACGC  CATCGCGAAA      60

TGGCAAAGAC  GACAAATGAA  ACACTCCAGG  CAATGGAAAT  CGATCGCCCG  ATGATTTATG     120

TTTACAACAA  AATGGATCAA  GTGAAAGACG  CGTTTCCTCA  AGCGCATGGC  ACGAGCTGTT     180

TATATCAGCT  AAGGCTAAAC  AAGGGCTTGA  TTTATTAGCA  CAGAAAATAG  CAAGCTATGT     240

TTTTCAAGAT  TTTGAAAAAC  ATCTGTTCAT  CATTCCTTAT  CGTGACGGGG  AGGCGGCTGC     300

TTATTTAAAC  AACCATGCCC  ATGTCCACAC  ACAGCGTGCT  GAGGAGGACG  GCTGGCATAT     360

CGTTGCCGAT  TTGCATGAAC  GAGACTTAAA  ACGGGTTGAA  AGCTACTGTG  TTTCAAAAGA     420

ACGATAATGA  AAAAAGCCAT  TTGAATGCTT  CTTGTTCAAA  TGGCTTTTTG  GCGACTATGG     480

TAGACAGATG  AACACTTGTT  TCGCTGTTTT  ACGACAAAGA  TCATCTTGCC  TGTTACGCGT     540

TTTTTAAATC  CGTTTTCGCA  CGTTCAATTG  TCGCCGAGTC  GTACCAGTCG  CTGTAAGTGA     600

GAATATGTTT  AGAAAGCCGC  GTATTTAAGC  GCAGTCTTTT  TCGTTCTGTA  CTGGCTGGTT     660

TGTGGACAGT  TTCCATACCC  ATCAACCTCC  TTTTATTTGT  AGCTTTCCCC  ACTTGAAACC     720

GTTTTAATCA  AAAACGAAGT  GAGAAGATTC  AGTTAACTTA  ACGTTAATAT  TTGTTTCCCA     780

ATAGGCAAAT  CTTTCTAACT  TTGATACGTT  TAAACTACCA  GCTTGGACAA  GTTGGTATAA     840

AAATGAGGAG  GGAACCGA  ATG AAG AAA  CCG TTG GGG  AAA ATT GTC  GCA AGC       891
```

-continued

|     |     |     |     |     | Met<br>-111 | Lys<br>-110 | Lys | Pro | Leu | Gly | Lys<br>-105 | Ile | Val | Ala | Ser |     |
|-----|-----|-----|-----|-----|-----|-----|-----|-----|-----|-----|-----|-----|-----|-----|-----|-----|
| ACC | GCA | CTA | CTC | ATT | TCT | GTT | GCT | TTT | AGT | TCA | TCG | ATC | GCA | TCG | GCT | 939 |
| Thr<br>-100 | Ala | Leu | Leu | Ile | Ser<br>-95 | Val | Ala | Phe | Ser | Ser<br>-90 | Ser | Ile | Ala | Ser | Ala<br>-85 |     |
| GCT | GAA | GAA | GCA | AAA | GAA | AAA | TAT | TTA | ATT | GGC | TTT | AAT | GAG | CAG | GAA | 987 |
| Ala | Glu | Glu | Ala | Lys<br>-80 | Glu | Lys | Tyr | Leu | Ile<br>-75 | Gly | Phe | Asn | Glu | Gln<br>-70 | Glu |     |
| GCT | GTC | AGT | GAG | TTT | GTA | GAA | CAA | GTA | GAG | GCA | AAT | GAC | GAG | GTC | GCC | 1035 |
| Ala | Val | Ser | Glu<br>-65 | Phe | Val | Glu | Gln | Val<br>-60 | Glu | Ala | Asn | Asp | Glu<br>-55 | Val | Ala |     |
| ATT | CTC | TCT | GAG | GAA | GAG | GAA | GTC | GAA | ATT | GAA | TTG | CTT | CAT | GAA | TTT | 1083 |
| Ile | Leu | Ser<br>-50 | Glu | Glu | Glu | Glu | Val<br>-45 | Glu | Ile | Glu | Leu | Leu<br>-40 | His | Glu | Phe |     |
| GAA | ACG | ATT | CCT | GTT | TTA | TCC | GTT | GAG | TTA | AGC | CCA | GAA | GAT | GTG | GAC | 1131 |
| Glu | Thr<br>-35 | Ile | Pro | Val | Leu | Ser<br>-30 | Val | Glu | Leu | Ser | Pro<br>-25 | Glu | Asp | Val | Asp |     |
| GCG | CTT | GAA | CTC | GAT | CCA | GCG | ATT | TCT | TAT | ATT | GAA | GAG | GAT | GCA | GAA | 1179 |
| Ala | Leu<br>-20 | Glu | Leu | Asp | Pro<br>-15 | Ala | Ile | Ser | Tyr | Ile<br>-10 | Glu | Glu | Asp | Ala | Glu<br>-5 |     |
| GTA | ACG | ACA | ATG | GCG | CAA | TCA | GTG | CCA | TGG | GGA | ATT | AGC | CGT | GTG | CAA | 1227 |
| Val | Thr | Thr | Met | Ala<br>1 | Gln | Ser | Val | Pro<br>5 | Trp | Gly | Ile | Ser | Arg<br>10 | Val | Gln |     |
| GCC | CCA | GCT | GCC | CAT | AAC | CGT | GGA | TTG | ACA | GGT | TCT | GGT | GTA | AAA | GTT | 1275 |
| Ala | Pro | Ala<br>15 | Ala | His | Asn | Arg | Gly<br>20 | Leu | Thr | Gly | Ser | Gly<br>25 | Val | Lys | Val |     |
| GCT | GTC | CTC | GAT | ACA | GGT | ATT | TCC | ACT | CAT | CCA | GAC | TTA | AAT | ATT | CGT | 1323 |
| Ala | Val | Leu<br>30 | Asp | Thr | Gly | Ile | Ser<br>35 | Thr | His | Pro | Asp | Leu<br>40 | Asn | Ile | Arg |     |
| GGT | GGC | GCT | AGC | TTT | GTA | CCA | GGG | GAA | CCA | TCC | ACT | CAA | GAT | GGG | AAT | 1371 |
| Gly | Gly | Ala | Ser<br>45 | Phe | Val | Pro | Gly<br>50 | Glu | Pro | Ser | Thr<br>55 | Gln | Asp | Gly | Asn<br>60 |     |
| GGG | CAT | GGC | ACG | CAT | GTG | GCC | GGG | ACG | ATT | GCT | GCT | TTA | AAC | AAT | TCG | 1419 |
| Gly | His | Gly | Thr | His<br>65 | Val | Ala | Gly | Thr<br>70 | Ile | Ala | Ala | Leu | Asn<br>75 | Asn | Ser |     |
| ATT | GGC | GTT | CTT | GGC | GTA | GCG | CCG | AGC | GCG | GAA | CTA | TAC | GCT | GTT | AAA | 1467 |
| Ile | Gly | Val | Leu<br>80 | Gly | Val | Ala | Pro | Ser<br>85 | Ala | Glu | Leu | Tyr<br>90 | Ala | Val | Lys |     |
| GTA | TTA | GGG | GCG | AGC | GGT | TCA | GGT | TCG | GTC | AGC | TCG | ATT | GCC | CAA | GGA | 1515 |
| Val | Leu | Gly<br>95 | Ala | Ser | Gly | Ser<br>100 | Gly | Ser | Val | Ser | Ser<br>105 | Ile | Ala | Gln | Gly |     |
| TTG | GAA | TGG | GCA | GGG | AAC | AAT | GGC | ATG | CAC | GTT | GCT | AAT | TTG | AGT | TTA | 1563 |
| Leu | Glu | Trp<br>110 | Ala | Gly | Asn | Asn | Gly<br>115 | Met | His | Val | Ala | Asn<br>120 | Leu | Ser | Leu |     |
| GGA | AGC | CCT | TCG | CCA | AGT | GCC | ACA | CTT | GAG | CAA | GCT | GTT | AAT | AGC | GCG | 1611 |
| Gly | Ser<br>125 | Pro | Ser | Pro | Ser<br>130 | Ala | Thr | Leu | Glu | Gln<br>135 | Ala | Val | Asn | Ser | Ala<br>140 |     |
| ACT | TCT | AGA | GGC | GTT | CTT | GTT | GTA | GCG | GCA | TCT | GGG | AAT | TCA | GGT | GCA | 1659 |
| Thr | Ser | Arg | Gly | Val<br>145 | Leu | Val | Val | Ala | Ala<br>150 | Ser | Gly | Asn | Ser | Gly<br>155 | Ala |     |
| GGC | TCA | ATC | AGC | TAT | CCG | GCC | CGT | TAT | GCG | AAC | GCA | ATG | GCA | GTC | GGA | 1707 |
| Gly | Ser | Ile | Ser<br>160 | Tyr | Pro | Ala | Arg | Tyr<br>165 | Ala | Asn | Ala | Met<br>170 | Ala | Val | Gly |     |
| GCT | ACT | GAC | CAA | AAC | AAC | AAC | CGC | GCC | AGC | TTT | TCA | CAG | TAT | GGC | GCA | 1755 |
| Ala | Thr | Asp | Gln<br>175 | Asn | Asn | Asn | Arg | Ala<br>180 | Ser | Phe | Ser | Gln<br>185 | Tyr | Gly | Ala |     |
| GGG | CTT | GAC | ATT | GTC | GCA | CCA | GGT | GTA | AAC | GTG | CAG | AGC | ACA | TAC | CCA | 1803 |
| Gly | Leu | Asp<br>190 | Ile | Val | Ala | Pro | Gly<br>195 | Val | Asn | Val | Gln | Ser<br>200 | Thr | Tyr | Pro |     |
| GGT | TCA | ACG | TAT | GCC | AGC | TTA | AAC | GGT | ACA | TCG | ATG | GCT | ACT | CCT | CAT | 1851 |
| Gly | Ser<br>205 | Thr | Tyr | Ala | Ser | Leu<br>210 | Asn | Gly | Thr | Ser | Met<br>215 | Ala | Thr | Pro | His<br>220 |     |
| GTT | GCA | GGT | GCA | GCA | GCC | CTT | GTT | AAA | CAA | AAG | AAC | CCA | TCT | TGG | TCC | 1899 |
| Val | Ala | Gly | Ala | Ala | Ala | Leu | Val | Lys | Gln | Lys | Asn | Pro | Ser | Trp | Ser |     |

STABILIZED ENZYMES AND PROCESS FOR PREPARING THEM

BACKGROUND OF THE INVENTION

The present invention relates to a process for improving the stability of enzymes toward ionic surfactants by directed mutagenesis of DNA sequences coding for these enzymes and subsequent expression of these enzymes with improved ionic surfactant stability.

Enzymes such as proteases, lipases, amylases, cellulases, etc. are valuable industrial products with advantageous applications in the detergent industry because they, for example, break down enzymatically cleavable contaminants and thus facilitate easier removal of these contaminants. In order to be effective, these enzymes must not only have enzymatic activity under washing conditions (pH, temperature), but must also be compatible with other detergent ingredients, especially, for example, with surfactants. That is to say, the enzymes must have sufficient stability and sufficient activity in the presence of these substances. In this regard it is particularly the surfactants of the ionic type, which are often used in detergent and cleaner compositions, which may adversely affect the stability of the enzymes used in detergents, so that the activity of the enzymes rapidly decreases in the presence of the ionic surfactant, and the enzyme activity can hardly be utilized adequately even with short washing cycles of about 30 minutes. This inadequate utilization of the enzymatic activity during the washing or cleaning process due to the lack of stability of the enzymes toward ionic surfactants, is unfortunately the cause of distinct reductions in the washing or cleaning efficiency. Good stability of the detergent and cleaner enzymes towards ionic surfactants is particularly necessary for liquid detergent and cleaner formulations because unlike the enzyme in powdered formulations, the enzymes in liquid formulations cannot be protected by coating processes against the destabilizing effects of other ingredients of the composition such as, in particular, ionic surfactants.

SUMMARY OF THE INVENTION

It was therefore the object of the invention to provide enzymes exhibiting improved stability toward the destabilizing effect of ionic surfactants.

A further object of the invention was to provide enzymes which particularly exhibited enhanced stability with respect to the action of anionic surfactants.

It was also an object of the invention to provide a process for stabilizing enzymes against the destabilizing effect of ionic surfactants.

These and other objects of the invention are achieved in accordance with the invention by providing an enzyme stabilized against the destabilizing effects of ionic surfactants, wherein at least one amino acid located in or in the direct vicinity of a hydrophobic surface region of the enzyme is replaced by a different amino acid whereby at least one of the following conditions (a), (b) and (c) is satisfied:

(a) a hydrophobic amino acid whose amino-acid residue is involved in the formation of a hydrophobic surface region in whose spatial vicinity at least one amino acid with an ionic amino acid residue is located is replaced by another amino acid having a hydrophilic amino acid residue;

(b) a polar uncharged amino acid which adjoins a hydrophobic surface region in whose spatial vicinity at least one amino acid with an ionic amino acid residue is located is replaced by an amino acid which is more sterically demanding than the polar uncharged amino acid, (c) an ionic amino acid which is located in the spatial vicinity of a hydrophobic surface region is replaced by an amino acid with an uncharged hydrophilic amino acid residue or by a charged amino acid whose amino acid residue has a charge in the same direction as the ionic surfactant.

In accordance with another aspect of the invention the objects are achieved by providing a process for improving the stability of an enzyme against the destabilizing effects of ionic surfactants, the process comprising replacing at least one amino acid located in or in the direct vicinity of a hydrophobic surface region of the enzyme by another amino acid whereby at least one of the following conditions (a), (b) and (c) is satisfied:

(a) a hydrophobic amino acid whose amino-acid residue is involved in the formation of a hydrophobic surface region in whose spatial vicinity at least one amino acid with an ionic amino acid residue is located is replaced by another amino acid with a hydrophilic amino acid residue, (b) a polar uncharged amino acid which adjoins a hydrophobic surface region in whose spatial vicinity at least one amino acid with an ionic amino acid residue is located is replaced by an amino acid which is more sterically demanding than the polar uncharged amino acid, (c) an ionic amino acid which is located in the spatial vicinity of a hydrophobic surface region is replaced by an amino acid with an uncharged hydrophilic amino acid residue or by a charged amino acid whose amino acid residue has a charge in the same direction as the ionic surfactant.

DETAILED DESCRIPTION OF PREFERRED EMBODIMENTS

The enzymes according to the invention are distinguished in that at least one of the amino acids located in a hydrophobic surface region of the enzyme or in the direct vicinity of this hydrophobic surface region is replaced by another amino acid whereby (a) a hydrophobic amino acid whose amino acid residue is involved in the formation of a hydrophobic surface region in whose spatial vicinity at least one amino acid with ionic amino acid residue is located is replaced by another amino acid with hydrophilic amino acid residue, and/or whereby (b) a polar uncharged amino acid which adjoins a hydrophobic surface region in whose spatial vicinity at least one amino acid with ionic amino acid residue is located is replaced by an amino acid which is more sterically demanding than the original amino acid, preferably by a more sterically demanding amino acid with a longer-chain hydrophilic amino acid residue, and/or whereby (c) an ionic amino acid which is located in the spatial vicinity of a hydrophobic surface region is replaced by an amino acid with an uncharged hydrophilic amino acid residue or by a charged amino acid whose amino acid residue has a charge in the same direction as the ionic surfactant.

In an advantageous embodiment of the invention, the enzymes present are ones in which the original amino acid according to (a), (b) and/or (c) is replaced in or at a hydrophobic surface region of the enzyme that exists in the form of a recess on the enzyme surface, especially a recess in the form of a hollow, a depression or a cavity penetrating into the interior of the enzyme. Without being bound to a particular theory, it is assumed that charged groups of ionic surfactants are attracted by regions on the enzyme surface having the opposite electrostatic charge and, due to electrostatic forces, enter into a first binding to the enzyme. It is also believed that, after this first binding of the ionic surfactant, the long-chain non-polar residue of the surfactant molecule can enter into a close interaction with accessible hydrophobic surface regions of the enzyme which are located in the immediate vicinity of the electrostatic binding site of the ionic surfactant. Interactions between the apolar surfactant residue and the hydrophobic surface region of the enzyme may result in denaturation of the enzyme and thus in its deactivation, especially when the hydrophobic region is in the form of a hollow, depression or cavity. This enables the apolar surfactant residue to gain access to the hydrophobic core of the enzyme unless the route for the apolar surfactant residue into the interior of the enzyme is blocked by stable structural elements of the enzymes such as, for example, a helix or a rigid fold etc. If the apolar surfactant residue, especially in the case of hydrophobic hollows, depressions or cavities, is able to easily penetrate through the hydrophobic surface region of the enzyme into its interior, it is probable that the enzyme will be unfolded and inactivated.

In preferred stabilized enzymes of the invention, the stability of the enzyme against the destabilizing effect of anionic surfactants is improved by an amino acid replacement according to (a) or (b) or by a replacement of a cationic amino acid by an amino acid with an uncharged hydrophilic or with an anionic amino acid residue.

The stabilized enzymes according to the invention can comprise any enzyme which can be employed in the detergent and cleaner industry, for example enzymes such as proteases, lipases, amylases, pullulanases, glucanases, pectinases, nucleases, oxidoreductases, etc. Particularly advantageous stabilized enzymes include proteases, lipases, amylases or cellulases. In one particularly preferred embodiment of the invention proteases are stabilized against the destabilizing effects of ionic surfactants. The invention is therefore described hereinafter in further detail using proteases as a representative example of the above-mentioned enzymes.

The so-called subtilisins are particularly advantageous as proteases. Subtilisins are alkaline serine proteases, i.e. proteases with a pH optimum in the alkaline pH range and with an essential serine residue in their active center. The subtilisins of the present invention can be obtained by cultivation of Gram-positive bacteria or fungi. Very well known prior art subtilisins can be obtained from Bacillus strains, for example subtilisins such as subtilisin BPN' or subtilisin Carlsberg. These also include alkaline proteases which can be obtained by cultivation of *Bacillus subtilis, Bacillus amyloliquefaciens, Bacillus licheniformis* or *Bacillus lentus*. Very particularly preferred subtilisins are the high-alkaline serine proteases which can be obtained, in particular, by cultivation of Bacillus species such as, for example, *Bacillus alcalophilus*.

In one specific embodiment of the invention, these high-alkaline proteases have an amino acid sequence with at least 80%, preferably at least 90%, and particularly preferably at least 95% homology with the amino acid sequence (SEQ ID NO:2) shown in FIG. 1, and with at least one of the original amino acids being replaced in the amino acid sequence of the high-alkaline protease by another amino acid as indicated under (a), (b) and/or (c).

As used herein, the term "homology" with the amino acid sequence (SEQ ID NO:2) shown in FIG. 1 is intended to refer to the structural relationship of the respective amino acid sequences to the amino acid sequence (SEQ ID NO:2) shown in FIG. 1. To determine the homology, each of the sections, which correspond structurally to one another, in the amino acid sequence (SEQ ID NO:2) of FIG. 1 and in the amino acid sequence to be compared therewith are brought into coincidence with one another so that there is maximum structural agreement between the amino acid sequences, taking into account any differences caused by deletion or insertion of individual amino acids and compensating by appropriate shifts of sequence sections. The number of amino acids which now agree with one another in the sequences ("homologous positions") related to the total number of amino acids contained in the sequence (SEQ ID NO:2) of FIG. 1 indicates the homology in % in this case. Differences in the sequences thus may be caused by variation, insertion and deletion of amino acids.

Accordingly it is apparent that when high-alkaline proteases which are at least 80% homologous with FIG. 1 (SEQ ID NO:2) are employed, the amino acid positions identified with reference to FIG. 1 (SEQ ID NO:2) relate to the positions which are homologous thereto in the protease employed in each case. Deletions or insertions in the amino acid sequences of the proteases homologous with FIG. 1 (SEQ ID NO:2) may result in relative shifts of the amino acid positions so that the numerical identifications of the amino acid positions which correspond to one another are not necessarily identical in homologous fragments of mutually homologous amino acid sequences.

Advantageously stabilized high-alkaline proteases of the invention include, in particular, those stabilized by replacement of amino acids in at least one of the positions 4, 14, 27, 39, 43, 47, 49, 77, 80, 89, 111, 117, 118, 127, 143, 161, 164, 165, 208, 232, 233, 235, 237, 249 or 256, preferably 27, 43, 118, 143, 164, 237, or 249, of FIG. 1 (SEQ ID NO:2) or in one of the positions homologous thereto. Of the above-mentioned replacement positions, positions 27, 43, 118, 143, 164, 237 and 249 of FIG. 1 (SEQ ID NO:2), and the positions homologous thereto are particularly advantageous. Examples of particularly preferred stabilized high-alkaline proteases include those which are stabilized by at least one of the following amino acid replacements: K27Q, I43R, I43K, I43Q, I43E, H118W, H118Y, R143N, R143S, R143T, R164Q, N237P, T249R, T249K, T249Q and T249E, with the positions referring to FIG. 1 (SEQ ID NO:2), or an amino acid replacement homologous thereto. The terminology used here to identify the mutations is customary in the art. The amino acids are identified by the one-letter code, and the original amino acid precedes the position indicator and the amino acid introduced for stabilization follows the position indicator.

According to the variant (a) of the invention, a hydrophilic amino acid is introduced in the enzymes in place of a hydrophobic amino acid in an apolar region of the enzyme surface. Within the scope of the invention, the replaced hydrophobic amino acids can be glycine (=Gly, G), alanine (=Ala, A), valine (=Val, V), leucine (=Leu, L), isoleucine (=Ile, I), phenylalanine (=Phe, F), proline (=Pro, P), especially the amino acids alanine, valine, leucine and isoleucine. The new hydrophilic amino acid entering in place of the original hydrophobic amino acid can have either a charged or an uncharged polar amino acid residue. Examples of hydrophilic amino acids with charged amino acid residue include the amino acids aspartic acid (=Asp, D), glutamic acid (=Glu, E), lysine (=Lys, K) and arginine (=Arg, R). Hydrophilic amino acids with an uncharged polar amino acid residue include, in particular, for example asparagine (=Asn, N) and glutamine (=Gln, Q). Particularly preferred are the longer-chain amino acids glutamine, glutamic acid, arginine and lysine. One example of a hydrophobic region in which an amino acid replacement according to (a) results in a stabilized high-alkaline protease from *Bacillus alcalophilus* is the hydrophobic region, depicted in FIG. 9, of amino acid position Ile 43. This hydrophobic region is surrounded by the polar amino acids Gln 57, Asn 42 and the ionic amino acid Arg 44. Replacement of Ile 43 in this hydrophobic region by, for example, arginine, lysine, glutamine or glutamic acid results in high-alkaline proteases stabilized according to the invention with one of the mutations I43R, I43K, I43Q and I43E.

According to variant (b) of the invention, an amino acid which is more sterically demanding than the original amino acid is introduced in the enzymes in place of a polar uncharged amino acid adjacent to the apolar region of the enzyme surface. The polar uncharged amino acids to be replaced for the purpose of this variant of the invention include, for example, the amino acids tyrosine, and, in particular, threonine, asparagine and histidine. Any amino acid which is sufficiently sterically demanding compared with the original amino acid is suitable for replacing the original amino acid according to variant (b) of the invention. In appropriate cases, even hydrophobic amino acids may be used to replace less sterically demanding amino acids. The more sterically demanding amino acid results in the apolar region being shielded from the destabilizing effect of the lipophilic surfactant residue so that the lipophilic surfactant residue is no longer able to penetrate into the hydrophobic interior of the enzyme. This variant of the invention is particularly suitable for shielding hydrophobic cavities from the destabilizing effect of a lipophilic surfactant residue. One example of variant (b) of the invention with a hydrophobic region in which replacement of an adjacent polar uncharged amino acid by a more sterically demanding amino acid results in a stabilized high-alkaline protease is depicted in FIG. 10. This hydrophobic region is in the form of a cavity which penetrates deeply into the hydrophobic interior of the enzyme and which is surrounded by a polar region formed by the amino acids His 118, Lys 229, Asn 237 and Arg 143. The polar uncharged amino acids His 118 and Asn 237 are directly adjacent to the hydrophobic region. Replacement of the amino acid His 118 or of the amino acid Asn 237 by a more sterically demanding amino acid, for example tryptophan, tyrosine or proline, results in a high-alkaline protease stabilized according to the invention with, for example, one of the mutations H118W, H118Y or N237P.

The apolar region of the enzyme surface is probably shielded in variant (b) of the invention by an amino acid which is more sterically demanding than the original amino acid and has a longer-chain hydrophilic amino acid residue. One example of a hydrophobic region of this type, in which replacement of an adjacent polar uncharged amino acid by a longer-chain hydrophilic amino acid results in a stabilized high-alkaline protease is depicted in FIG. 11. This hydrophobic region is formed by the amino acids Leu 261 and Val 262 and is surrounded by a polar region composed of the amino acids Glu 265, Asn 263, Gln 12, Arg 10, Asn 178. The polar uncharged amino acid which is adjacent to the hydrophobic region at Leu261-Val262 is Thr 249. Replacement of the amino acid Thr 249 by, for example, one of the longer-chain hydrophilic amino acids arginine, lysine, glutamine or glutamic acid results in high-alkaline proteases stabilized according to the invention with, for example, one of the mutations T249R, T249K, T249Q, and T249E.

According to variant (c) of the invention an uncharged hydrophilic amino acid or an amino acid which is charged to the surfactant is introduced in place of an ionic amino acid which is situated in the vicinity of an apolar region of the enzyme surface and whose charged amino acid residue can form a point of attachment for the ionic surfactant. In this case the ionic amino acids which are to be replaced and the amino acids which are charged in the same direction as the surfactant, within the meaning of the invention are the hydrophilic amino acids having charged amino acid residues which have already been mentioned above, i.e. aspartic acid, glutamic acid, lysine and arginine. In enzymes which are stabilized toward cationic surfactants, one of the anionic amino acids such as aspartic acid and glutamic acid is replaced by a cationic amino acid such as lysine or arginine. On the other hand, in enzymes which are stabilized according to this variant of the invention toward anionic surfactants, a cationic amino acid such as lysine or arginine is replaced by an anionic amino acid. In another preferred embodiment of variant (c) of the invention, however, the ionic amino acid to be replaced is replaced by an uncharged hydrophilic amino acid. Uncharged hydrophilic amino acids for this preferred embodiment include, in particular, the amino acids serine (=Ser, S), threonine (Thr, T), asparagine (=Asp, N), glutamine (=Gln, Q) and tyrosine (=Tyr, Y). The amino acids with shorter polar amino acid residues, such as serine, threonine and particularly asparagine, are preferred when the charge on the original ionic amino acid of the enzyme projects far into the surrounding medium. The replacement of the original ionic amino acid by an uncharged hydrophilic amino acid results in enzymes which are stabilized against the effects of both cationic and anionic surfactants. One example of a hydrophobic region of the enzyme surface in which an amino acid replacement according to variant (c) of the invention results in a stabilized high-alkaline protease from *Bacillus alcalophilus* is depicted in FIG. 12. This hydrophobic region is in the form of a cavity which penetrates deeply into the hydrophobic interior of the enzyme and is surrounded by the amino acids Glu 110, Asn 114 and Arg 143. Replacement of the ionic amino acid Arg 143, which can form a preferred point of attachment for an anionic surfactant, by, for example, asparagine, serine or threonine results in high-alkaline proteases stabilized according to the invention with, for example, one of the mutations R143N, R143S or R143T.

Examples of high-alkaline proteases stabilized according to the invention and described above include those obtainable by cultivation of microorganisms such as, for example, *Bacillus alcalophilus*. In particular, these high-alkaline Bacillus proteases can be obtained by cultivation of Bacillus species which have the identifying characteristics of *Bacillus alcalophilus* DSM 5466. The stabilized proteases of the invention thus are related, as defined by the homology described above, to the protease obtainable from *Bacillus alcalophilus* DSM 5466 having the amino acid sequence indicated in FIG. 1 (SEQ ID NO:2) which serves as a point of reference for the proteases stabilized according to the invention. These high-alkaline proteases have molecular weights of 26,000 to 28,000 g/mole, as measured by SDS polyacrylamide gel electrophoresis in comparison with reference proteins of known molecular weight. They are furthermore distinguished by a pH optimum in the range from 10 to 12.5. As used herein, the term "pH optimum" refers to that pH range in which the proteases have maximum proteolytic activity and the proteases have a good pH stability.

The enzymes stabilized according to the invention and described above can be prepared by the stabilizing process of the invention. This process for improving the stability of enzymes against the destabilizing effects of ionic surfactants is characterized in that at least one of the amino acids located in a hydrophobic surface region of the enzyme or in the direct vicinity of this hydrophobic surface region is replaced by another amino acid whereby (a) a hydrophobic amino acid whose amino-acid residue is involved in the formation of a hydrophobic surface region in whose spatial vicinity at least one amino acid with ionic amino acid residue is located is replaced by another amino acid with hydrophilic amino acid residue, and/or whereby (b) a polar uncharged amino acid which adjoins a hydrophobic surface region in whose spatial vicinity at least one amino acid with ionic amino acid residue is located is replaced by an amino acid which is more sterically demanding than the original amino acid, preferably by a more sterically demanding amino acid with a longer-chain hydrophilic amino acid residue, and/or whereby (c) an ionic amino acid which is located in the spatial vicinity of a hydrophobic surface region is replaced by an amino acid with an uncharged hydrophilic amino acid residue or by a charged amino acid whose amino acid residue has a charge in the same direction as the ionic surfactant.

In the process according to the invention, amino acids in the amino acid sequence of the respective enzyme to be stabilized are replaced in accordance with the guidelines of process variants (a), (b) and/or (c), by directed mutagenesis of the DNA sequence which codes for the amino acid sequence of the enzyme. The subsequent expression of the mutated DNA sequence by means of a suitable microorganism then provides the stabilized enzyme according to the invention by amino acid replacement. The specific procedure for carrying out the process in this case can be such that a) initially the DNA sequence coding for the enzyme (i.e. the structural gene of the enzyme) is isolated from a suitable microorganism which produces the enzyme to be stabilized;

b) the nucleotide sequence of this DNA sequence is determined;

c) mutations are generated in the determined DNA sequence so that the mutated DNA sequence now codes for an enzyme in which an amino acid of the original enzyme is replaced according to the guidelines of process variants (a), (b) and/or (c) by another amino acid;

d) subsequently the mutated DNA sequence is incorporated into a suitable expression vector;

e) the resulting expression vector is used to transform a suitable microorganism which can finally be employed to produce the mutated enzyme.

The individual process steps for the stabilization according to the invention and for obtaining the enzymes stabilized according to the invention, as well as the products obtained thereby and intermediates in the form of DNA sequences, vectors, particularly expression vectors, and transformed microorganisms are described in detail hereinafter with reference to the example of the high-alkaline proteases. Analogous procedures can be used for stabilizing other enzymes, for example lipases, amylases, cellulases etc., in accordance with the invention.

To prepare high-alkaline proteases stabilized according to the invention, initially the DNA sequence coding for the protease (that is to say the structural gene of the protease) is isolated from a suitable bacterium which produces a high-alkaline protease with an amino acid sequence having at least 80%, preferably at least 90%, and particularly preferably at least 95%, homology with the amino acid sequence of FIG. 1 (SEQ ID NO:2). The structural genes which code for amino acid sequences of these high-alkaline proteases can be obtained by generally known methods. For this purpose, for example, the chromosomal DNA is isolated by known methods from a bacterium ("donor bacterium"), in particular from a Bacillus species which produces the high-alkaline protease, and is partially hydrolysed in a known manner with suitable restriction endonucleases. The resulting restriction fragments of the donor DNA can be fractionated according to size, for example by gel electrophoresis, and the fragments of required size can then be ligated (connected) to a suitable doublestranded vector DNA in vitro (recombination). Commonly used vectors include plasmids (i.e. extrachromosomal, circular, double-stranded bacterial DNA) which can be introduced by suitable methods (transformation) into microorganisms and can replicate there (capable of autonomous replication). If desired, the plasmids may contain markers (i.e. DNA fragments which code for certain observable properties such as antibiotic resistance) which can be used to select the transformed microorganisms (transformants).

The above-mentioned plasmids (composed of vector DNA plus restriction fragments of the donor DNA) can be used to transform bacteria, preferably a Bacillus species, and the transformants can be selected by the known marker property (for example neomycin resistance). In this way clones (i.e. genetically identical transformants) are obtained. The transformants among these which exhibit increased expression of protease can be sought on protein-containing plates and then isolated. Finally, the plasmid DNA introduced in these transformants is isolated from a clone with protease activity, and renewed transformation of a bacterium is carried out to check whether the protease activity is plasmid-bound, i.e. whether the protease activity is coupled to the marker property.

The plasmid isolated in this way contains, besides the vector DNA with known restriction sites, the required structural gene for the initial high-alkaline protease to be stabilized and other DNA sequences, which are not, however, required here, from the donor bacterium. In order to minimize the effort required for subsequent sequencing of the structural gene of the high-alkaline protease to be stabilized, it is advisable before the actual sequencing to eliminate the additional unrequired DNA sequences from the donor DNA sequence and to reduce the donor DNA sequence essentially to the structural gene for the protease. In order to achieve this, for example, the plasmid which comprises the structural gene and the additional DNA sequence is cut with a plurality of various restriction endonucleases (restricted), the resulting DNA fragments are separated according to size by gel electrophoresis, and a restriction map is constructed based on the observed band pattern. In this way the restriction sites situated in the region of the donor DNA sequence are identified. Knowledge of the restriction map of the plasmid makes it possible, by cutting with selected restriction endonucleases, to cut out of the donor DNA sequence a DNA fragment which essentially comprises only the structural gene for the high-alkaline protease, the relevant pre and pro units, and the promoter unit necessary for gene expression.

Reincorporation of this donor DNA sequence which has been reduced in size into a suitable vector makes it possible to obtain a new replicable vector whose ability to express the initial high-alkaline protease can be checked by transforming a bacterium, especially a Bacillus species, with this vector, cultivating the resulting transformant and checking for protease activity. One example of a reduced vector of this type, called pCLEAN4, is depicted in the restriction map in FIG. 2.

To determine the nucleotide sequence of (i.e. to sequence) the protease structural gene, the vector described above is initially replicated in a suitable microorganism, and the protease gene is isolated. The protease gene is then subcloned into a phagemid, and the resulting phagemids are subsequently transformed into a suitable microorganism, for example E. coli, and single-stranded DNA containing the protease gene is produced by cultivation of the transformants. The single-stranded DNA which is formed is isolated and subjected to sequencing. The sequencing may be carried out by known methods, for example by subjecting the single-stranded DNA with the protease gene to a base-specific partial chemical cleavage by the method of Maxam and Gilbert (1980, in Methods in Enzymology, Grossmann L., Moldave K., eds., Academic Press Inc., New York and London, Vol. 65, 499), or, for example by employing the single-stranded DNA with the protease gene as template for the partial synthesis of fragments of the complementary DNA strand by the dideoxy chain-terminator method of Sanger et al. (1977, Proc. Natl. Acad. Sci. USA 74: 5463).

The determined nucleotide sequence can now be translated with the aid of the genetic code (one triplet word= codon stands for a defined amino acid) into the amino acid sequence of the protease. To determine the starting point of the amino acid sequence of the mature protease enzyme (that is to say the enzyme without the pre and pro units), a short piece of the amino acid sequence at the N-terminal end of the mature protease is analyzed by known methods for determining the amino acid sequences in peptides. The known N-terminal amino acid sequence can now be assigned on the basis of the genetic code to the appropriate fragment of the above nucleotide sequence, and thus the starting point of the DNA sequence coding for the mature protease can be established. The subsequent amino acid sequence of the protease then emerges automatically from the DNA sequence by assignment of the subsequent amino acids using the genetic code.

The DNA sequence coding for the high-alkaline protease is mutated according to the invention by modifying the appropriate codons in such a way that the mutated DNA sequence codes for a high-alkaline protease which is stabilized against the effect of ionic surfactants and in whose amino acid sequence the relevant amino acid in one of the positions 4, 14, 27, 39, 43, 47, 49, 77, 80, 89, 111, 117, 118, 127, 143, 161, 164, 165, 208, 232, 233, 235, 237, 249 or 256 of FIG. 1 (SEQ ID NO:2), or in one of the positions homologous thereto, is replaced by an amino acid according to one of process variants (a), (b) and/or (c).

The introduction of the mutations into the DNA coding for the high-alkaline protease is effected by known methods for directed mutagenesis. In order to accomplish this, circular single-stranded DNA which contains the complete structural gene, or else, preferably, only that part (for example only the N-terminal part or the C-terminal part) of the structural gene of the original protease in which the mutation is to be carried out, is generated from suitable vectors (phagemids), for example from pCLMUTN1 of FIG. 4 or pCLMUTC1 of FIG. 5, optionally by using a helper phage. This circular single-stranded DNA is used to hybridize a synthetic oligonucleotide which is capable of hybridization and which contains in the required mutation site a base triplet (codon) which, instead of coding for the original amino acid to be replaced, codes according to the invention for a new amino acid, according to (a), (b) or (c). In addition, the oligonucleotide is also modified, by one or a few more nucleotide units, compared with the original nucleotide sequence to be hybridized, in such a way that although the coding of the original amino acid sequence is retained within the scope of the degeneracy of the genetic code, a restriction site present in the original protease nucleotide sequence is deleted in the synthetic oligonucleotide, or another restriction site is introduced into the synthetic oligonucleotide. The deleted or introduced restriction site is subsequently used to identify the mutant DNA sequence by using suitable restriction endonucleases and comparing the result with the original DNA sequence. The partially double-stranded DNA sequence obtained by hybridization is made up to the complete double strand by adding the required nucleotides in the presence of DNA polymerase and DNA ligase. The resulting circular double-stranded DNA sequence is subsequently used as a vector to transform a suitable microorganism and, after sufficient replication, the mutated DNA sequences are identified via the deleted or additionally introduced restriction site in the oligonucleotide sequence part and are subsequently isolated.

In one process variant, uracylated single-stranded DNA is generated in the directed mutagenesis as a template and is used for the hybridization with the synthetic oligonucleotides. After completion of the reactions of the process of directed mutagenesis, the uracil-containing single strand DNA, which was used as template for generating mutated DNA strands (vectors), can be eliminated by treatment with uracil N-glucosylase without the need for phenotypical selection of mutants. The glucosylase treatment can be carried out by using, for example, a suitable microorganism which has uracil N-glucosylase activity and which has been transformed with mutated vector DNA. Replication can take place, for example, in an E. coli strain which replicates only the mutated non-uracylated DNA strand of the double-stranded vector generated in the mutation process. This additionally facilitates the selection of the mutated DNA vectors.

The synthetic oligonucleotides required for directed mutagenesis are prepared by known methods. For example, the oligonucleotides can be prepared by the method of Beaucage S. L. and Caruthers M. H. (1981, Tetrahedron Letters 22:1859–1862) with β-cyanoethyl phosphoramidite in a Cyclone synthesizer (Biosearch). The resulting oligonucleotides can be purified, for example, by elution from polyacrylamide gels and, optionally subsequent desalting with the aid of Sephadex columns, and can then be used further. The synthetic oligonucleotides can be used directly as primers for the DNA polymerase in the mutagenesis process described above. The synthetic oligonucleotide sequences comprise, for example, 20 to 30 nucleotide units which code for about 7 to 10 amino acids. It is, of course, also possible to employ longer nucleotide sequences for the hybridization described above, but this does not have any further advantages as long as it is ensured that the short-chain synthetic oligonucleotides are sufficiently hybridizable.

The circular double-stranded DNA sequences with the introduced mutations obtained by the above-described process of directed mutagenesis represent mutated vectors from which, depending on the case, the complete mutated protease structural gene or the mutated fragment of the protease structural gene can be cut out by treatment with suitable restriction endonucleases, and can be inserted into a suitable expression vector (subcloned). This expression vector is then used to transform suitable microorganisms, for example, Bacillus species, which are then cultured under suitable conditions for the expression and recovery of the mutated high-alkaline proteases.

In one preferred embodiment of the process, the complete structural gene is not employed for the directed mutagenesis but only a fragment thereof in which the mutation is to be generated. In order to accomplish this, for example, the N-terminal or C-terminal half of the structural gene is cut out with suitable restriction endonucleases from the vector used for replication of the structural genes, and is subcloned into an appropriate phagemid. This results in vectors which contain either the N-terminal or the C-terminal half of the structural gene of the protease and which are initially sufficiently replicated in a suitable microorganism, for example E. coli, and then subjected to the directed mutagenesis described above. Mutagenesis of fragments of the structural gene has the advantage that shorter single-stranded DNA sequences can be used and thus, after the hybridization step with synthetic oligonucleotides, considerably fewer nucleotides have to be replenished in the partial DNA double strand than when the complete DNA sequence is used. The synthetic effort and also the risk of unwanted random mutations are thereby reduced.

The mutated DNA sequences can be cut out of the cloning vectors used for generating the mutations by suitable restriction endonucleases and incorporated into vectors with appropriate restriction sites. The resulting vectors are, for example, precursors of the actual expression vectors required for the expression of the high-alkaline protease. The structures of these vectors are such that besides the suitable restriction sites (for example from a synthetic linker), they also already contain the regulatory sequences, signal sequences and promoter sequences which are required for protease expression in a host organism, and the DNA sequences coding for the pre and pro units of the protease.

Subcloning a mutated DNA sequence into a vector of this type results in the actual expression vector for an optimized high-alkaline protease. Incorporation of the mutated DNA sequence into this precursor of the expression vector is carried out so that an expression vector with suitable reading frame is produced. In this case it is possible to incorporate mutated fragments of the DNA sequence coding for the protease, for example a C-terminal or an N-terminal fragment, into vectors already containing the remaining non-mutated fragment, or the complete mutated DNA sequence coding for the protease is incorporated into vectors which do not yet contain fragments of this protease DNA sequence. Examples of such precursor vectors of an expression vector, which already contain a fragment of the non-mutated DNA sequence, include the vectors called pAL1N and pAL1C which are described in detail hereinafter and in the examples. A vector which does not yet contain a fragment of the protease DNA sequence is the vector pAL1P which has the restriction map shown in FIG. 7.

The expression vector precursors for the preferred variant of the invention (mutation in the N-terminal half or in the C-terminal half) are obtained, for example, as follows. Initially, a polycloning site is introduced into a Bacillus plasmid. The resulting plasmid is restricted and recombined with an E. coli plasmid fragment which contains markers and sequence parts needed for replication. Where appropriate, restriction sites which would interfere with subsequent process steps are deleted, for example by directed mutagenesis. A new vector is constructed from the resulting plasmid which contains the DNA sequences from the BaciHus plasmid and the E. coli plasmid used for replication, DNA sequences for the promoter, DNA sequences which code for the pre-pro sequence of the protease (obtained from, for example, the plasmid pCLEAN4 of FIG. 2), and a synthetic linker. An example of a plasmid of this type, called pAL1P, is depicted in the restriction map of FIG. 7. The synthetic linker in this case is selected so that, after cutting with suitable restriction endonucleases, recombination is possible either with the complete original structural gene or with the complete mutated structural gene or with mutated or non-mutated fragments of the structural gene. To prepare an expression vector precursor which is to be recombined, for example, with a mutated N-terminal half of the structural gene, the non-mutated C-terminal half of the structural gene of the protease is initially introduced into the vector constructed above, which contains the aforementioned Bacillus, E. coli, promoter and pre and pro sequences of the protease and the synthetic linker, by cutting the synthetic linker, for example. The vectors of the pAL1C type which have already been mentioned are obtained in this way. Subsequently, the mutated N-terminal half of the protease structural gene which is missing as yet is introduced by cutting the synthetic linker once more. A vector of the pAL1NC type shown in FIG. 8 is obtained in this way.

The converse case is analogous. In this case the non-mutated N-terminal half is initially introduced into a vector of the pAL1P type to obtain a pAL1N type vector, and the mutated C-terminal half is subsequently introduced into the pAL1N vector to obtain a vector of the pAL1NC type as shown in FIG. 8.

The expression vectors described above are used to transform suitable bacteria, preferably Bacillus species, especially *Bacillus subtilis, B. licheniformis* and *B. alcalophilu*. The transformants are subsequently cultured in a known manner and the resulting high-alkaline protease stabilized according to the invention is isolated from the culture medium. For this purpose, the expression vectors can be transformed either into bacteria which are still capable of producing their own native protease or into protease-deficient bacteria (which no longer produce their own native protease). In the case of host organisms which produce their own native protease, the high-alkaline protease stabilized according to the invention can, if required, be freed of the native proteases which are produced, by subsequent purification operations, for example by high performance liquid chromatography (HPLC). In contrast, a purification step of this type can be omitted if protease-deficient host organisms are used because such organisms are able to produce only (or essentially only) the stabilized protease.

The process according to the invention for stabilizing enzymes against the destabilizing effects of ionic surfactants also results in new DNA sequences to which the invention likewise relates. These DNA sequences according to the invention are characterized in that they code for a high-alkaline protease with an amino acid sequence which has at least 80%, preferably at least 90%, and particularly preferably at least 95%, homology with the amino acid sequence shown in FIG. 1 (SEQ ID NO:2), and differs from the latter in at least one of positions 4, 14, 27, 39, 43, 47, 49, 77, 80, 89, 111, 117, 118, 127, 143, 161, 164, 165, 208, 232, 233, 235, 237, 249 or 256, preferably 27, 43, 118, 143, 164, 237 or 249, of FIG. 1 (SEQ ID NO:2) or in one of the positions homologous thereto, which are located in a hydrophobic surface region of the protease or in the vicinity of this hydrophobic surface region, in that the amino acid located in the relevant position in the case of positions with (a) a hydrophobic amino acid whose amino-acid residue is involved in the formation of a hydrophobic surface region in whose spatial vicinity at least one amino acid with ionic amino acid residue is located is replaced by another amino acid with hydrophilic amino acid residue, and/or that in the case of positions with (b) a polar uncharged amino acid which adjoins a hydrophobic surface region in whose spatial vicinity at least one amino acid with ionic amino acid residue is located is replaced by an amino acid which is more sterically demanding than the original amino acid, preferably by a more sterically demanding amino acid with a longer-chain hydrophilic amino acid residue, and/or that in the case of positions with (c) an ionic amino acid which is located in the spatial vicinity of a hydrophobic surface region is replaced by an amino acid with an uncharged hydrophilic amino acid residue or by a charged amino acid whose amino acid residue has a charge in the same direction as the ionic surfactant.

Positions of hydrophobic amino acids which are located in the hydrophobic region of the enzyme surface include, for example., Val 4, Pro 14, Pro 39, Ile 43, Ala 47, Phe 49, Ile 77, Leu 80, Trp 111, Met 117, Pro 127, Pro 233, Trp 235, and Leu 256. Positions of polar uncharged amino acids which are adjacent to a hydrophobic region of the enzyme surface include, for example, the tyrosine positions 89, 161, 165, 208; the asparagine positions 232 and 237; the histidine position 118 and the threonine position 249. Examples of positions of ionic amino acids which are in the vicinity of a hydrophobic region include, in particular, the arginine positions 143 and 164 and the lysine position 27.

The enzymes stabilized according to the invention are outstandingly suitable, individually or in combination with one another or with other enzymes known in the state of the art, for use in solid and liquid detergent and cleaner formulations, particularly for use in liquid formulations. These detergent and cleaner formulations can be formulated in a customary manner. For this purpose the enzymes stabilized according to the invention can be mixed, for example in the form of granules, prills or pellets, optionally also provided with surface coatings or in the case of liquid formulations also in dissolved form, with the other components of the detergent and cleaner formulation in a known manner. The enzymes stabilized according to the invention can be employed in the formulations in customary amounts for detergent and cleaner enzymes, especially in amounts of up to 3% by weight (based on the dry matter of the complete composition), preferably in an amount of 0.2 to 1.5% by weight. The invention therefore furthermore includes detergent and cleaner formulations which contain at least one enzyme stabilized according to the invention; and particularly those formulations which contain enzymes according to the invention and ionic surfactants, especially anionic surfactants. Besides the enzymes according to the invention, the detergent and cleaner formulations can also contain known enzymes and customary detergent ingredients known in the art, such as surfactants, bleaches or builders, as well as customary amounts of other conventional detergent additives. Such additives include, for example, enhancers, enzyme stabilizers, soil carriers and/or compatibilising agents, complexing and chelating agents, soap foam regulators and additives such as optical brighteners, opacifying agents, corrosion inhibitors, antistatic agents, dyes, bactericides, bleach activators, and/or peracid bleach precursors.

By way of example, typical detergent and cleaner formulations according to the invention may contain, based on dry matter a) at least 5% by weight, for example 10 to 50% by weight, of an ionic, preferably anionic, surfactant or of a mixture of such surfactants;

b) up to 40% by weight of a builder or a builder mixture;

c) up to 40% by weight of a bleach or bleach mixture, preferably a perborate such as sodium perborate tetrahydrate or sodium perborate monohydrate;

d) up to 3% by weight of at least one enzyme according to the invention, in particular a protease according to the invention;

e) other constituents such as additives, fillers, etc. to make up to 100% by weight.

BRIEF DESCRIPTION OF THE DRAWINGS

The invention will be described in further detail with reference to non-limiting preferred embodiments illustrated in the accompanying drawings, wherein:

FIG. 1 is a sequence listing for the DNA sequence (SEQ ID NO:1) of the AvaI/HindIII fragment of the structural gene for the initial high-alkaline protease from *Bacillus alcalophilus* HA1, and the amino acid sequence (SEQ ID NO:2) of this initial protease;

FIG. 3 shows examples of DNA sequences of synthetic oligonucleotides (SEQ ID NOs. 3–18) used for directed mutagenesis in which eliminated and generated recognition sites for individual restriction endonucleases are indicated, and the nucleotide modifications generated by comparison with the original DNA sequence (SEQ ID NO:1) of the initial protease are identified by depicting the modified nucleotides with small letters;

EXAMPLES

Figure 2:
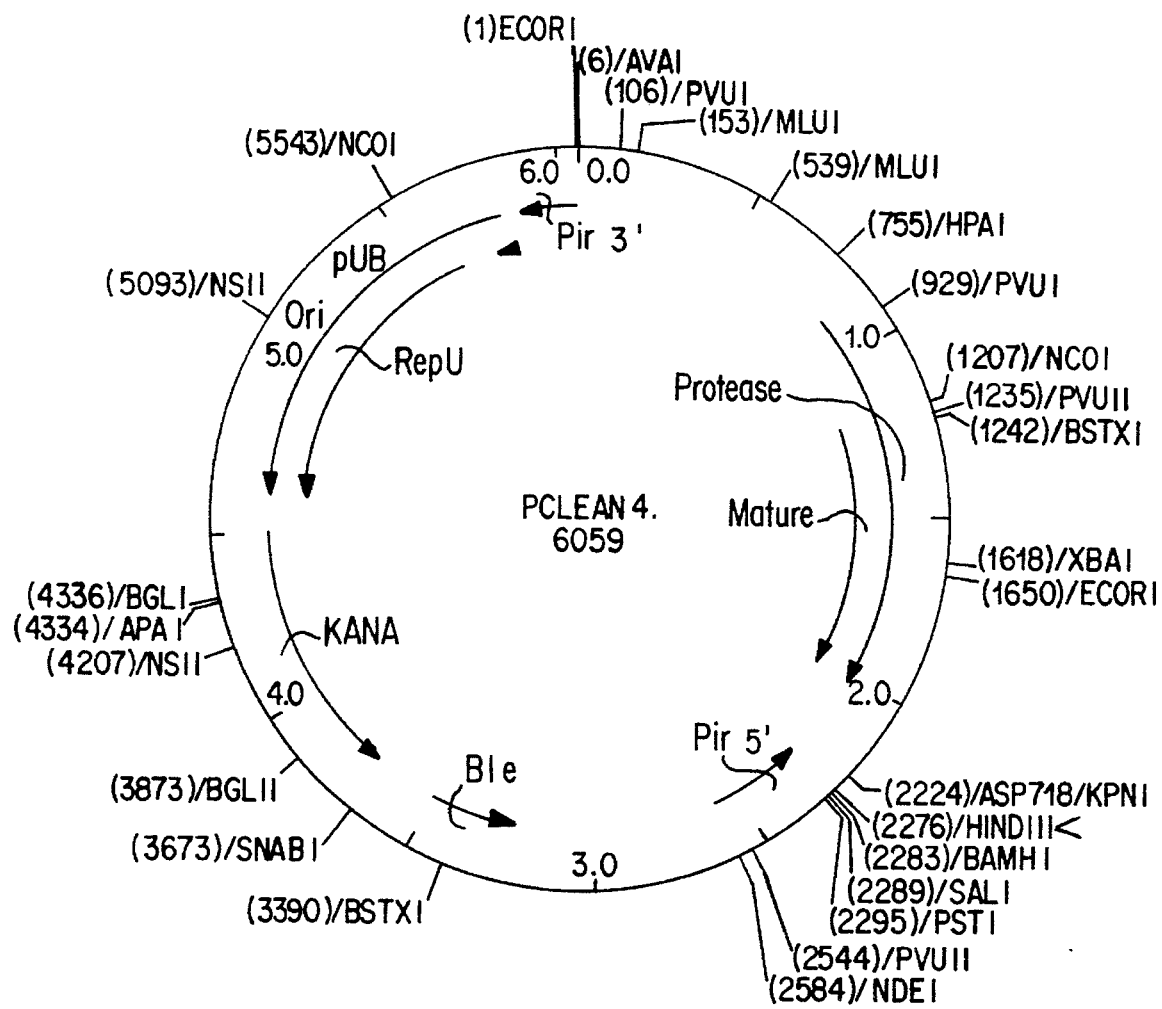
FIG. 2 is a restriction map of the plasmid pCLEAN4.

The following disclosure describes, for further explanation of the invention, typical exemplary embodiments of the invention based on the example of a high-alkaline protease from *Bacillus alcalophilus* HA1, but without restricting the invention thereby.

In order to simplify the examples, some frequently recurring methods and terms are explained in detail hereinafter and then referred to in the individual examples only in abbreviated fashion. Unless otherwise indicated, the methods generally used were those described in Maniatis et al., *Molecular Cloning, A Laboratory Manual*, Cold Spring Harbor Laboratory (1982).

Initial vectors used here are commercially available on an unrestricted basis, or they can be prepared by known methods from available vectors. For example, pBS phagemids (for example pBS(+), pBS(−) etc.) are commercially available from Stratagene, La Jolla, Calif.; the helper phage M13K07 from Bio-Rad Laboratories, Richmond, Calif.; the vector M13tg131 from Amersham, Buckinghamshire, England, and the plasmid pUC18 from Pharmacia LKB, Uppsala, Sweden.

The various restriction endonucleases used are known in the art and are commercially available. The reaction, cofactor and other conditions needed for the use of each of these known restriction endonucleases are likewise known.

The cutting of vectors with restriction endonucleases can, where appropriate, be followed by a hydrolysis of the terminal 5'-phosphate residue with an alkaline phosphatase (dephosphorylation). It is possible in this way to prevent the ends produced on cutting of the restricted vector from recombining with each other which otherwise could prevent the required insertion of a foreign DNA fragment into the restriction site. In the examples, dephosphorylation of the 5' end was carried out in a known manner. Further details of the dephosphorylation procedure and the required reagents therefor are found in Maniatis et al. (pp. 133–134).

As used herein, the term "partial hydrolysis" refers to incomplete digestion of DNA by a restriction endonuclease. In this case the reaction conditions were selected so that there was cutting at some, but not all, of the recognition sites in the DNA substrate for the restriction endonuclease used.

To obtain and isolate certain DNA fragments, for example after treatment of DNA with restriction endonucleases, the resulting DNA fragments were separated in a known manner by gel electrophoresis (for example on an agarose gel), subsequently identified via the molecular weight (determined by comparison with reference DNA fragments of known molecular weight), and the required DNA fragments were recovered from the appropriate gel zones.

Treatment with the Klenow fragment of DNA polymerase I from *E. coli* refers to a process for filling in the internal 3' ends of double-stranded DNA with nucleotides which are complementary to the nucleotides of the particular protruding 5' ends of the DNA double strand. The Klenow fragment, and the reagents required for the Klenow treatment are known in the art and are commercially available. Details of the Klenow treatment can be found, for example, in Maniatis et al. (pp. 107–108).

The term "ligation" refers to a process for forming phosphodiester linkages between DNA fragments (see, for example, Maniatis et al., pp. 146). Ligation can be carried out under known conditions, for example in a buffer with about 10 units of T4 DNA ligase per 0.5 µg of an approximately equimolar amount of the DNA fragments to be ligated.

The term "transformation" refers to the insertion of DNA into a microorganism so that the DNA can be replicated and expressed therein. Suitable methods for transformation of *E. coli* include, for example, the calcium chloride method of Mandel et al. (1970, J. Mol. Biol. 53: 159) or of Maniatis et al. (pp. 250 to 251). The method of Anagnostopoulos et al. (1961, J. Bact. 81: 741–746) is suitable for Bacillus species, for example.

The term "linker" refers to a short-chain double stranded DNA fragment which has some recognition sites for restriction endonucleases and is suitable for joining DNA fragments. Linkers are used, for example, in recombining DNA fragments to give a vector and can be employed to introduce particular recognition sites for restriction endonucleases into this vector.

A "polycloning site" (polylinker) is a short to medium double-stranded DNA fragment which has in the near vicinity a plurality of recognition sites for restriction endonucleases. A polycloning site used in the examples which derives from the vector M13tg131 has, for example, a size of about 0.07 KB (kilo base-pairs) and contains has recognition sites for fourteen different restriction endonucleases.

The *Bacillus alcalophilus* strain employed in Example 1, which is called *Bacillus alcalophilus* HA1, was deposited at the Deutsche Sammlung von Mikroorganismen on 28 Jul. 1989 (DSM 5466). Other microorganisms used can be purchased, for example Bacillus subtilis BD 244 (Bacillus Genetic Stock Center 1 A 46) or Bacillus subtilis BD 366 (Bacillus Genetic Stock Center 1 E 6).

Example 1

Preparation of a genomic DNA library of *B. alcalophilus* and isolation of the gene for its high-alkaline protease.

Chromosomal DNA was isolated by the method of Saito et al. (1963, Biochim. Biophys. Acta. 72: 619-629) from the natural isolate *Bacillus alcalophilus* HA1 (deposited at the Deutsche Sammlung von Mikroorganismen under the number DSM 5466) and was partially hydrolysed with the restriction endonuclease Sau3A. The restriction fragments were fractionated by electrophoresis on an agarose gel, and the fragments with a size of 3 to 8 kilobases (KB) were isolated.

The isolated and size-selected DNA fragments from *Bacillus alcalophilus* HA1 were recombined in vitro with vector DNA of the plasmid pUB 110 (obtained as described in Example 7). To accomplish this the plasmid pUB110 was initially restricted with the restriction endonuclease BamHI and subsequently dephosphorylated with alkaline phosphatase from calf intestine. Subsequently 2 µg of the restricted and dephosphorylated vector DNA were incubated with 8 µg of the *Bacillus alcalophilus* DNA fragments in a total volume of 100 µl with T4 DNA ligase at 16° C. for 24 hours.

The resulting in vitro recombined DNA was used to transform protoplasts of the strain *Bacillus sibto;os* BD224 by the method described by S. Chang and N. Cohen (1979, Mol. Gen. Genet. 168:111–115). The transformants were selected on plates with neomycin and subsequently transferred to skimmed milk agar. From 13,800 tested transformants, one was found which produced a distinctly larger zone due to proteolysis of the skimmed milk agar. The plasmid DNA was isolated from this clone as described by Maniatis et al. The cloned fragment from the *B. alcalophilus* DNA contained in this plasmid had a size of 4.1 KB and contained the complete information for the high-alkaline protease from *Bacillus alcalophilus* HA1.

To simplify the subsequent process, the DNA fragment 4.1 KB in size was initially reduced in size. This was accomplished by determining the recognition sites located on the DNA fragment for restriction endonucleases by cutting the plasmid with various restriction endonucleases and fractionating the fragments of restricted DNA by electrophoresis on an agarose gel. A DNA fragment 2.3 KB in size obtained by cutting with the restriction endonucleases AvaI and HindIII was found to have the complete information for the high-alkaline protease and was used for the subsequent process. To accomplish this, the above plasmid with the 4.1 KB fragment was restricted with the restriction endonucleases AvaI and HindIII. The DNA fragment 2.3 KB in size was isolated and ligated to the vector pUB131 (obtained as described in Example 7) which had likewise previously been cut with AvaI and HindIII.

The resulting plasmid, which was called pCLEAN4, was inserted into the strain *B. subtilis* BD224. The transformants were able to express the high-alkaline protease, which shows that the AvaI/HindIII fragment contains the complete structural gene for the high-alkaline protease from *B. alcalophilus* HA1. The restriction map of the plasmid pCLEAN4 is depicted in FIG. 2.

Example 2

Sequencing of the structural gene of the high-alkaline protease from *B.alcalophilus*.

To prepare single-stranded DNA of the protease structural gene, the plasmid pCLEAN4 was cut with the restriction endonucleases AvaI and HindIII, and the AvaI/HindIII DNA fragment about 2.3 KB in size (protease structural gene) was inserted into the phagemid pBS (+) or pBS (−). The nucleotide sequence of the protease gene contained in the isolated single-stranded phagemids was determined by the dideoxy chain-terminator method of Sanger et al. (1977, Proc. Natl. Acad. Sci. USA 74:5463) and the method of base-specific chemical cleavage of the DNA single-strand described by Maxam et al. (1980, in Methods in Enzymology, Grossmann L., Moldave K., eds., Academic Press Inc., New York and London, Vol. 65, 499). The nucleotide sequence which was determined and the assigned amino acid sequence of the protease are depicted in FIG. 1 (SEQ ID NO:1). The start of the amino acid sequence (amino acid residues 1–269 of (SEQ ID NO:2) of the mature high-alkaline protease in position 1190 of the nucleotide sequence (SEQ ID NO:1) was determined by amino acid sequencing of the N-terminal end of the high-alkaline protease.

Example 3

Preparation of mutated DNA sequences by directed mutagenesis.

The directed mutations were carried out in DNA partial sequences of the protease structural gene using the primer extension technique described by Kunkel, T.A. (1985, Proc. Natl. Acad. Sci. USA 82:488–492). The plasmids pCLMUTN1 (prepared as described in Example 4) and pCLMUTC1 (prepared as described in Example 5) were used for this after each had initially been converted as described hereinafter into their uracylated, single-stranded analogs. The initial vectors pCLMUTN1 and pCLMUTC1 do not contain the complete DNA sequence of the protease structural gene from *B. alcalophilus* HA1, but instead contain only the N-terminal half (pCLMUTN1) or the C-terminal half (pCLMUTC1) thereof.

As derivatives of a phagemid, these vectors are capable to a certain extent of forming single-stranded vector DNA which under the given conditions could be secreted by the host organism used for replication and then isolated.

Each of these vectors was introduced by the $CaCl_2$ method of Maniatis et al. (pp. 250 to 251) into *E. coli* CJ236 as host organism. Since the bacterium *E. coli* CJ236 (uracil N-glycosylase-deficient mutant) incorporates the nucleotide uracil in place of thymine into the DNA sequence of the vector when the vector is replicated, culturing the above transformants resulted in the uracil-containing analogs of the vector pCLMUTN1 or pCLMUTC1. These uracil-containing vectors cannot be distinguished from the usual thymine-containing vectors in vitro reactions. The uracil content in the vector DNA does not interfere with in vitro DNA syntheses, since uracil is not mutagenic either in vitro or in vivo, and uracil codes in the same way as thymine. Uracylated vectors can be employed advantageously for the subsequent in vitro reactions of directed mutagenesis. After the reactions are complete, the uracil-containing single strand DNA, which was used as a template for generating mutated DNA strands (vectors), can be eliminated by treatment with uracil N-glycosylase without the need for phenotypical selection of mutants. The glycosylase treatment can be carried out both with the isolated enzyme and with an *E coli* strain which has been transformed by vector DNA and has uracil N-glycosylase activity.

The uracylated single-stranded DNA of the vectors pCLMUTN1 and pCLMUTC1 required as a template for the directed mutagenesis was prepared by cultivating *E. coli* CJ236 bacteria which had been transformed with one of the two vectors and which had additionally been infected with helper phage M13K07.

The helper phage itself is scarcely capable of replication and shows no interfering interaction with the vector DNA of the vectors pCLMUTN1 or pCLMUTC1. Its task is to synthesize coating proteins for the uracylated single-stranded vector DNA which is formed. Coated single-stranded vector DNA is secreted by the host organism *E. coli* CJ236 and can be isolated from the culture medium. With the assistance of the helper phage there is a considerable increase in the qualitative and quantitative yield of (in this case uracylated) single-stranded vector DNA.

The isolated uracylated DNA single-stranded vectors pCLMUTN1 or pCLMUTC1 were hybridized with the synthetic oligonucleotides which were prepared as in Example 6 and which contained a mutation site and simultaneously acted as primers for the subsequent replenishment of the complete DNA double-strand with mutation.

The second DNA strand was synthesized by adding nucleotides and T4 DNA polymerase and subsequently ligating of the newly formed strand with T4 DNA ligase (Kunkel et al. 1987, Methods in Enzymol. 154, 367–382). The double-stranded vector DNA which was formed was transformed into *E. coli* MC1061, and the mutated vectors were identified by checking for the presence or absence of the appropriate unique restriction endonuclease recognition sites which were introduced or deleted with the synthetic oligonucleotides.

Example 4

Construction of the vector pCLMUTN1.

Figure 4:
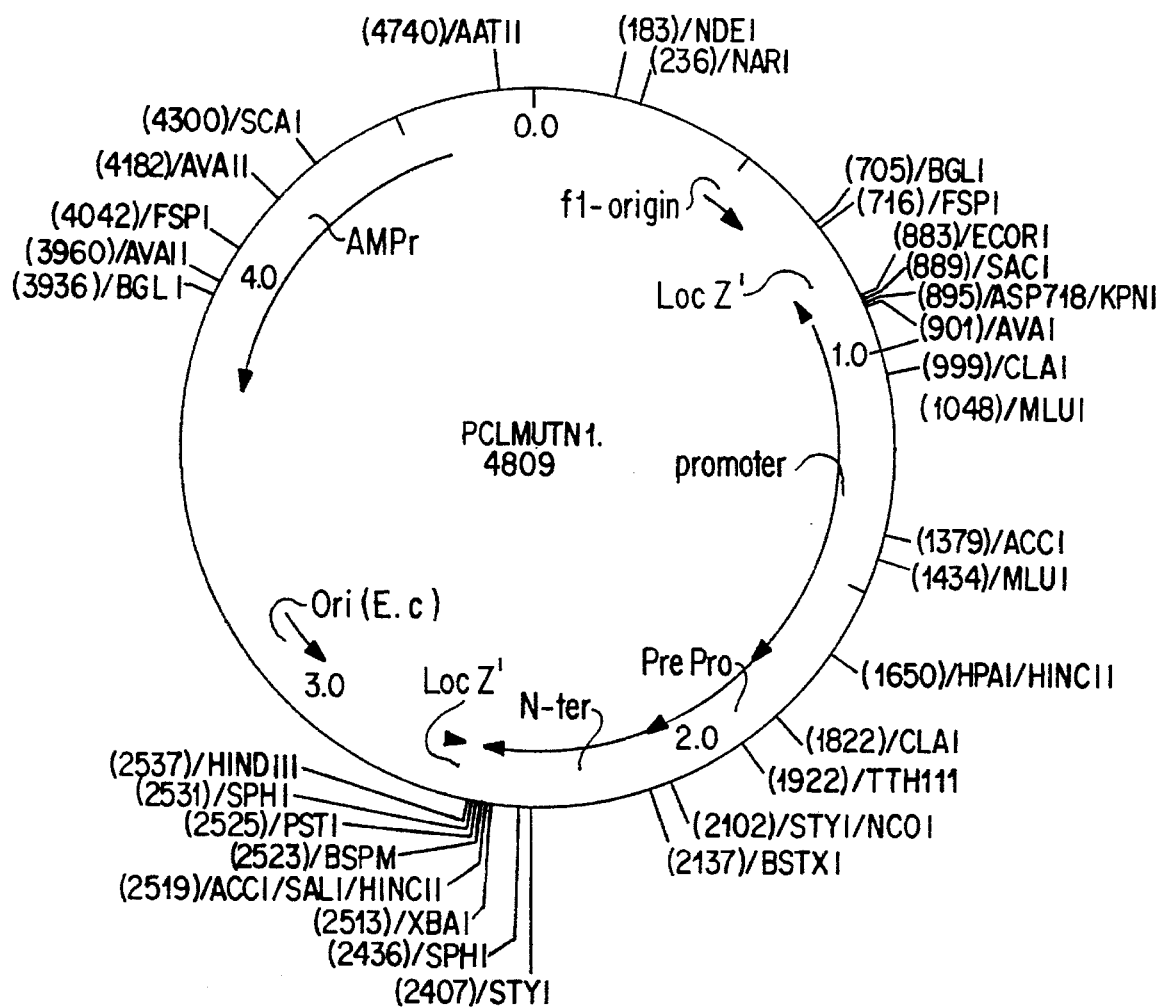
FIG. 4 is a restriction map of the vector pCLMUTN1.

The plasmid pCLEAN4 prepared in Example 1 was cut with AvaI. The protruding ends (sticky ends) were filled in with the aid of the Klenow fragment of *E. coli* DNA polymerase I (Maniatis et al., pp. 114) with addition of the required nucleotides to give the DNA double strand. After subsequent restriction of this DNA with XbaI, the N-terminal fragment comprising 1618 base pairs (BP) of the protease gene was isolated and cloned into the SmaI/XbaI site of pBS. The resulting vector was called pCLMUTN1. The restriction map of this vector is depicted in FIG. 4.

Example 5

Construction of the vector pCLMUTC1.

Figure 5:
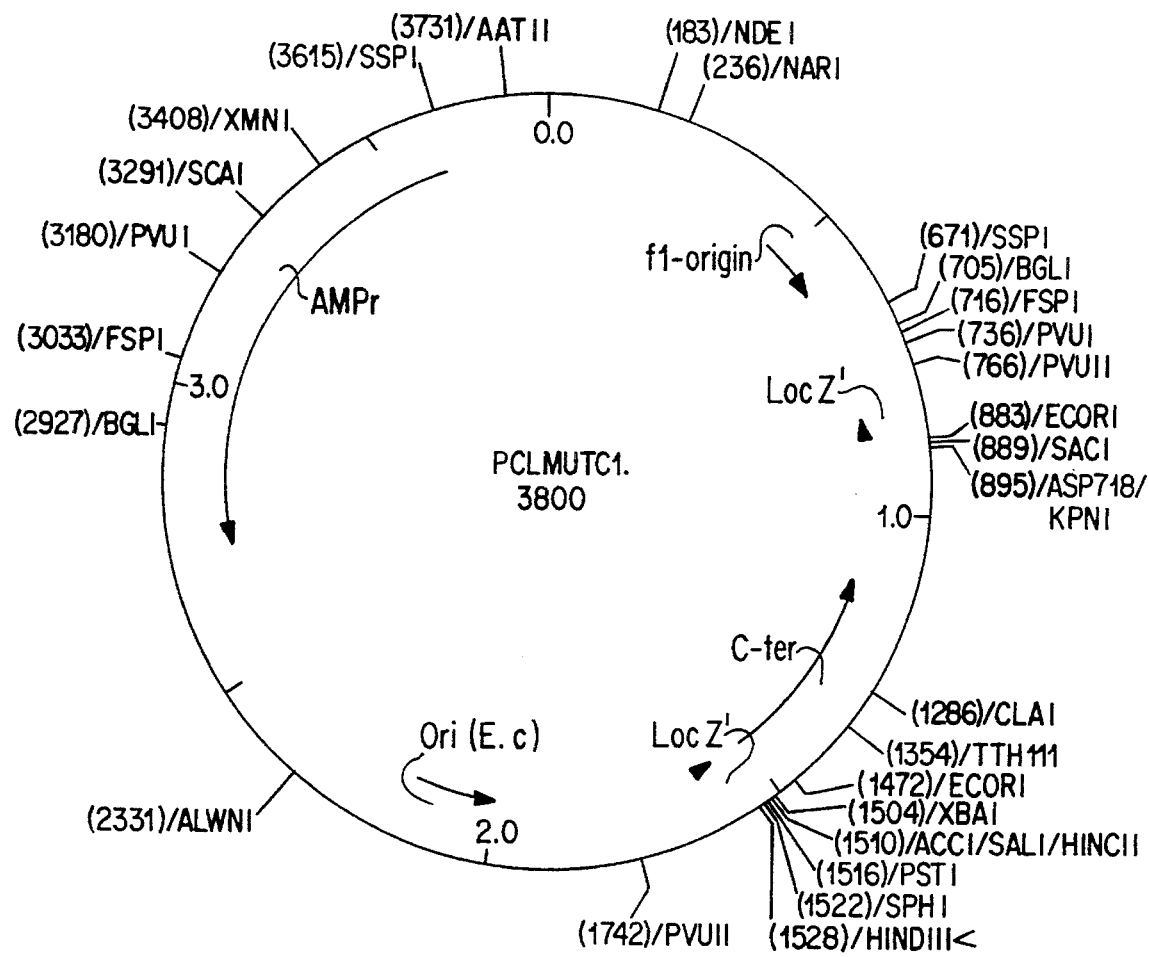
FIG. 5 is a restriction map of the vector pCLMUTC1.

The plasmid pCLEAN4 prepared in Example 1 was cut with the restriction endonucleases XbaI and Asp718. The XbaI/Asp718 double-stranded DNA fragment which comprises 658 base pairs and which embraces the C-terminal half of the protease structural gene was cloned into the XbaI/Asp718 site of pBS. The resulting vector was called pCLMUTC1. The restriction map of the vector is depicted in FIG. 5.

Example 6

Synthesis of artificial oligonucleotides for directed mutagenesis.

Synthetic oligonucleotides were prepared by the method of Beaucage S. L. and Caruthers M. H. (1981, Tetrahedron Letters 22: 1859–1862) with β-cyanoethyl phosphoramidite in a Cyclone synthesizer (Biosearch). The resulting oligonucleotides were purified by elution from polyacrylamide gels and subsequent desalting using Sephadex G25 columns. Examples of the synthesized nucleotide sequences and their properties are reproduced in FIG. 3 (SEQ ID NOs 3–18). The sequences of the synthetic oligonucleotides used in the process of Example 3 for introducing the mutations into the protease gene were selected so that they met the following conditions.

The DNA sequence of the synthetic oligonucleotides was still sufficiently complementary to the corresponding sequence of the protease gene to ensure an adequate hybridization ability thereof.

Replacement of one or more nucleotides within the codon which codes for the amino acid to be replaced by other nucleotides so that this mutated codon now coded for an amino acid with a more voluminous and/or ionic amino acid residue (mutations). The codon employed for the new amino acid was the one most frequently found in the protease gene for the relevant amino acid.

Replacement of other nucleotides within other codons so that although the DNA still coded for the same amino acids, restriction endonuclease recognition sequences in the protease gene were deleted or newly generated. These served in the process of Example 3 to facilitate the screening for the vectors with the mutated DNA sequences for the new high-alkaline proteases.

Example 7

Isolation and purification of the plasmid pUB110 and construction of the vector pUB131.

The plasmid pUB110 was isolated from the strain *Bacillus subtilis* BD366 by the method of T. J. Gryczan et al. (1978, J. Bacteriol. 134: 318–329) and subsequently purified by caesium chloride density gradient centrifugation as described by Maniatis et al. (pp. 93). The vector pUB110 contains a restriction site, which occurs only once, for the restriction endonuclease BamHI, a marker DNA sequence which codes for antibiotic resistance to neomycin, and DNA sequences required for replication in Bacillus species (origin of replication).

The plasmid pUB110 obtained above was restricted with EcoRI and BamHI. The smaller segment (790 BP) was replaced by a polylinker which consisted of 67 base pairs previously isolated as an EcoRI/BglII fragment from the vector M13tg131. The resulting vector called pUB131 is thus a derivative of pUB110 in which the EcoRI/BamHI fragment about 0.8 KB in size has been deleted and, instead, a polycloning site has been inserted.

Example 8

Construction of the vectors pUBC131 and pUBC132.

The plasmid pUC18 was cut with AatII and PvuII. The fragment 1990 base pairs in size containing the β-lactamase gene and the *E. coli* origin of replication was isolated. The protruding ends (sticky ends) were filled in with the aid of the Klenow fragment of *E. coli* DNA polymerase I (Maniatis et al., pp. 114) with addition of the required nucleotides to yield the DNA double strand. The fragment was subsequently inserted into the SnaBI site of the vector pUB131 obtained as in Example 7, resulting in the vector called pUBC131.

The 2187 BP EcoRI/BglII fragment of the vector pUBC131 obtained above was subcloned into the EcoRI/BamHI site of pBS (+), resulting in the vector called pBSREPU. Subsequently the NcoI or StyI recognition site which is present in the DNA sequence for the repU polypeptide in the vector pBSREPU (I. Maciag et al. 1988, Mol. Gen. Genet. 212: 232–240) was eliminated by directed mutagenesis by replacing the nucleotide sequence CCA TGG by the nucleotide sequence CCG TGG (both nucleotide sequences code for the amino acid sequence tryptophan-proline). The procedure was analogous to the procedure of Example 3. This was accomplished by preparing uracylated single-stranded DNA of the vector pBSREPU as a template for the directed mutation to eliminate the NcoI or StyI recognition site. This template was subsequently replenished analogously to the primer extension technique described in Example 3, using the following synthetic oligonucleotide (SEQ ID NO:20)

Figure 6:
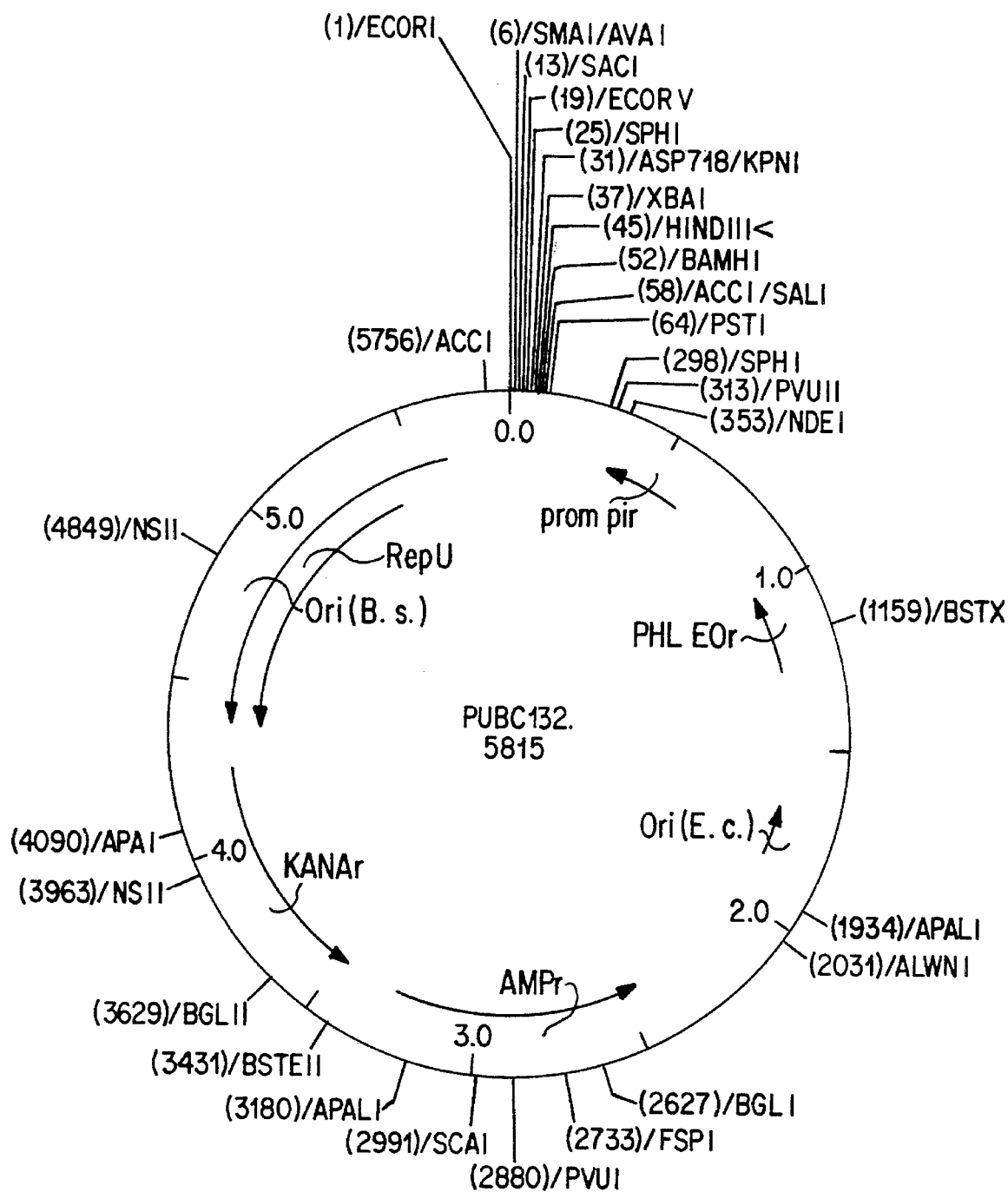
FIG. 6 is a restriction map of the vector pUBC132.

```
                                    NcoI/StyI
Original repU                       Pro  Trp
sequence (SEQ ID NO: 19): AAA GTG AGA CCA TGG AGA GAA AA
Synthetic repU
sequence (SEQ ID NO: 20): AAA GTG AGA CCg TGG AGA GAA AA
``` to give the DNA double-stranded vector, and the vectors which were now free of NcoI and StyI recognition sites were isolated by transformation and cultivation of *E. coli* MC1061. The 1726 BP EcoRI/ApaI fragment of the isolated vector was introduced into the EcoRI/ApaI site of pUBC131. The new vector, whose restriction map is depicted in FIG. 6, was called pUBC132.

Example 9

Construction of the plasmid pAL1P.

The plasmid pAL1P was prepared by ligation of the following three elements:

the 2218 base pair AvaI/NcoI fragment of pCLEAN4, containing the promoter and the pre-pro region of the initial high-alkaline protease.

the following synthetic linker with single recognition sites for the restriction endonucleases NcoI, XbaI and Asp718, which make it possible to introduce the mutated N-terminal or C-terminal halves of the protease gene from the mutated vectors pCLMUT1 and pCLMUTC1 or to introduce the complete gene of the initial protease from the plasmid pCLEAN4;

(SEQ ID NO: 21) 5' - CCATGGTCTAGAGGTACCA- 3'
(SEQ ID NO: 22)       3' - CAGATCTCCATGGTTCGAA - 5'
                         ∧  ∧      ∧       ∧
                        NcoI XbaI  Asp718
                                        HindIII The above double-stranded synthetic linker with protruding 5' ends was prepared by initially preparing and purifying separately each of the two single-stranded DNA sequences analogously to the synthesis of the synthetic oligonucleotides in Example 6. The resulting single strands were subsequently hybridized together to give the double strand.

the 5776 base pair AvaI/HindIII fragment from the vector pUBC132 prepared in Example 8, containing DNA sequences for replication and selectable markers in *E. coli*, as well as DNA sequences for replication and selectable markers in *B. subtilis, B. licheniformis* and *B. alcalophilus*.

Figure 7:
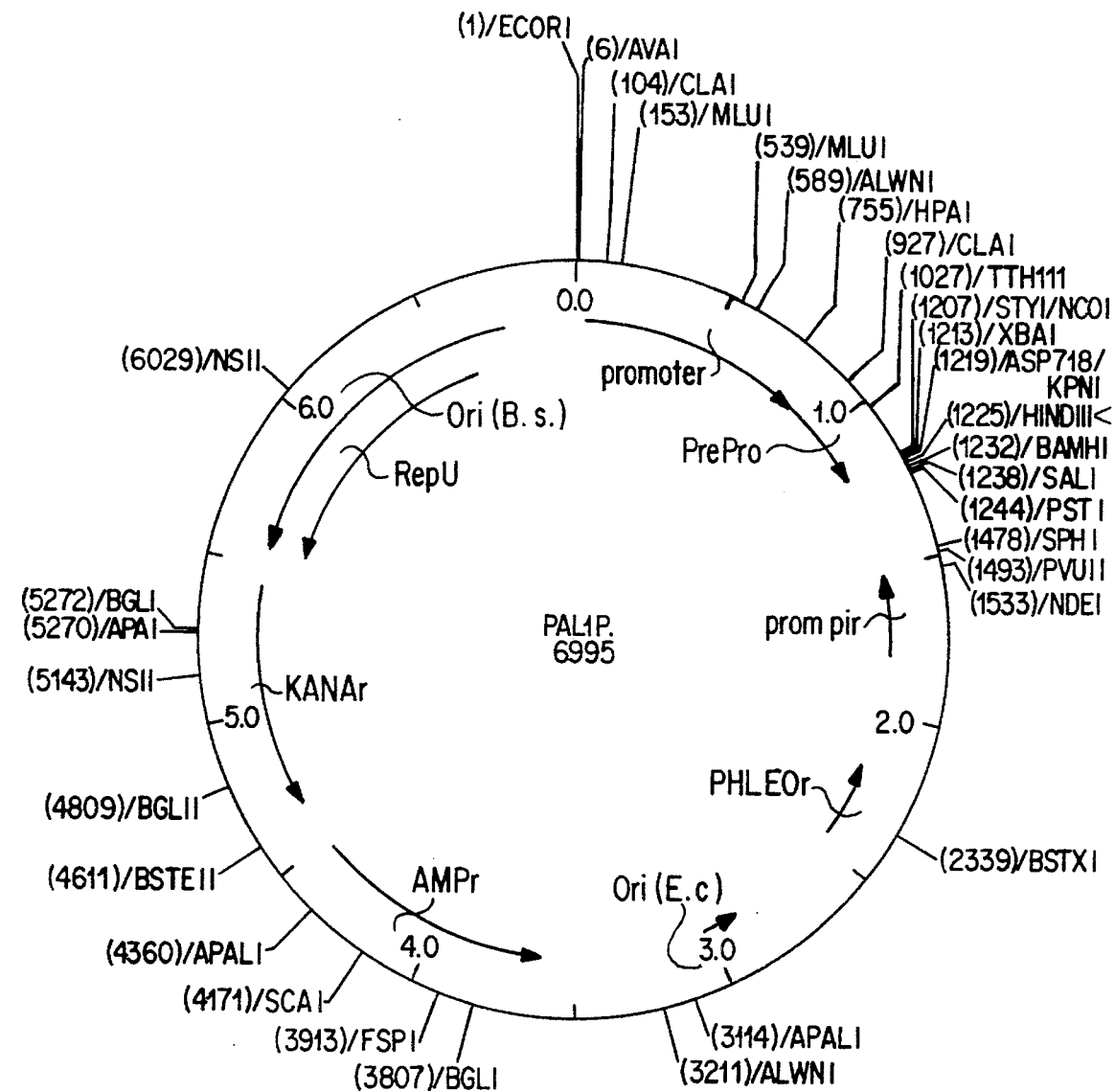
FIG. 7 is a restriction map of the plasmid pAL1P.

The construction of the vector pAL1P was carried out in *E. coli* MC1061, and the vector was isolated from ampicillin-resistant *E. coli* transformants. The restriction map of the resulting vector is depicted in FIG. 7.

Example 10

Construction of the plasmids pAL1N and pAL1C.

The construction of the vectors pAL1N and pAL1C was carried out in *E. coli* MC1061, and the vectors were isolated from ampicillin-resistant *E. coli* transformants.

The plasmid pAL1N was constructed, by initially cutting the vector pCLEAN4 obtained in Example 1 with the restriction endonucleases NcoI and XbaI, and subsequently cloning the resulting NcoI/XbaI fragment into the NcoI/XbaI site of the vector pAL1P (prepared as in Example 9). The prepared vector contained the N-terminal part of the DNA sequence which codes for the mature enzyme, and the regulatory elements for transcription and translation of the high-alkaline protease, as well as the signal sequence and the processing sequence.

The plasmid pAL1C was constructed by initially cutting the vector pCLEAN4 obtained in Example 1 with the restriction endonucleases XbaI and Asp718, and cloning the resulting XbaI/Asp718 fragment into the XbaI/Asp718 site of the vector pAL1P (prepared as in Example 9). The prepared vector contained the C-terminal part of the DNA sequence which codes for the mature protease, and the regulatory elements for transcription and translation of the high-alkaline protease, as well as the signal sequence and the processing sequence.

Example 11

Construction of the expression vectors pAL1NC.

Expression vectors with mutations in the C-terminal part of the protease DNA sequence, expression vectors with mutations in the N-terminal part of the protease DNA sequence and, for the purposes of comparison, also expression vectors without mutations in the protease DNA sequence were prepared.

Figure 8:
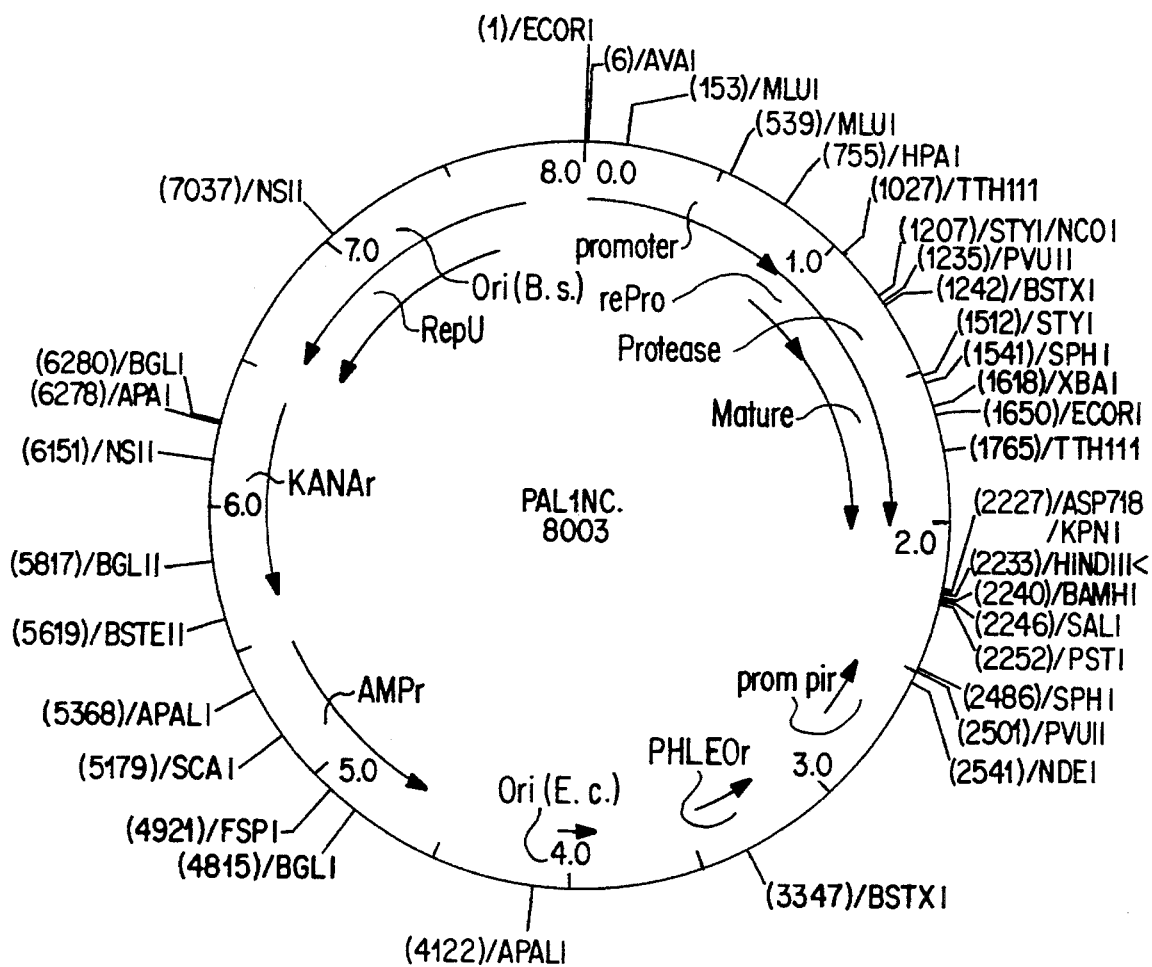
FIG. 8 is a restriction map of the expression vectors of the pAL1NC type for expressing the high-alkaline proteases stabilized by mutation and the non-mutated initial high-alkaline protease.
Figure 9:
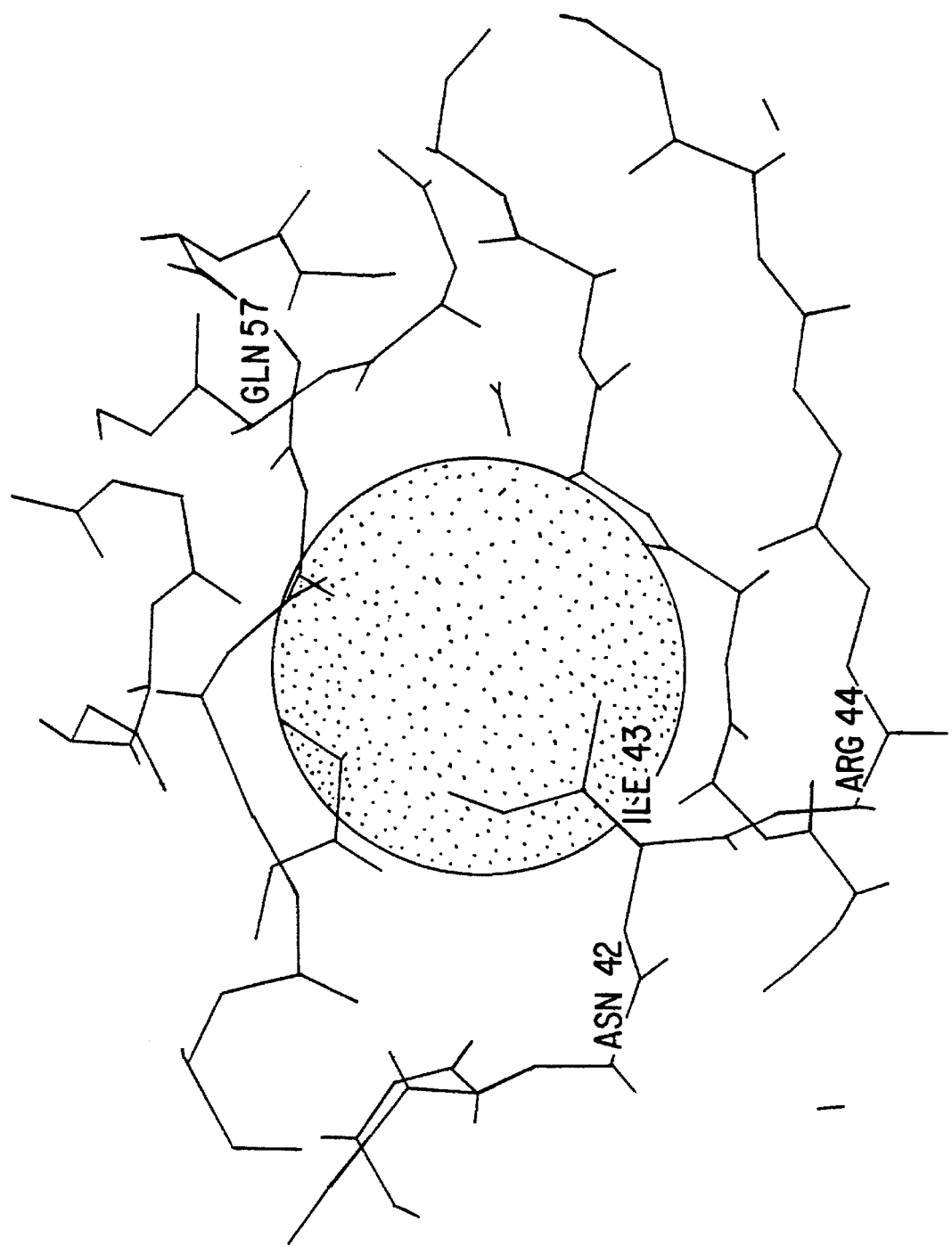
FIG. 9 shows a flat hydrophobic region at position Ile 43.
Figure 10:
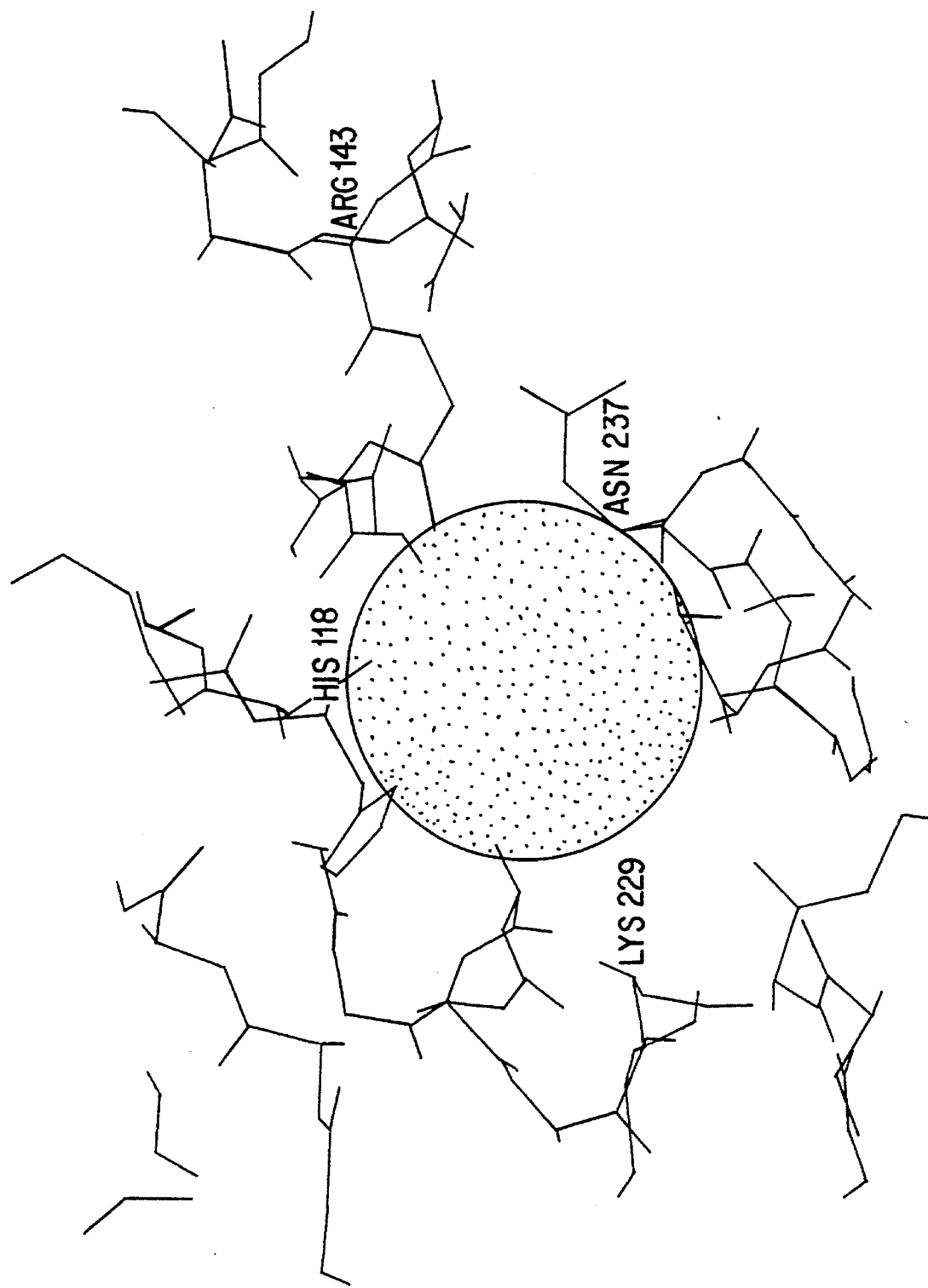
FIG. 10 shows a hydrophobic cavity which penetrates deeply into the interior of the enzyme and to which the replaceable polar uncharged amino acids His 118 and Asn 237 are adjacent.
Figure 11:
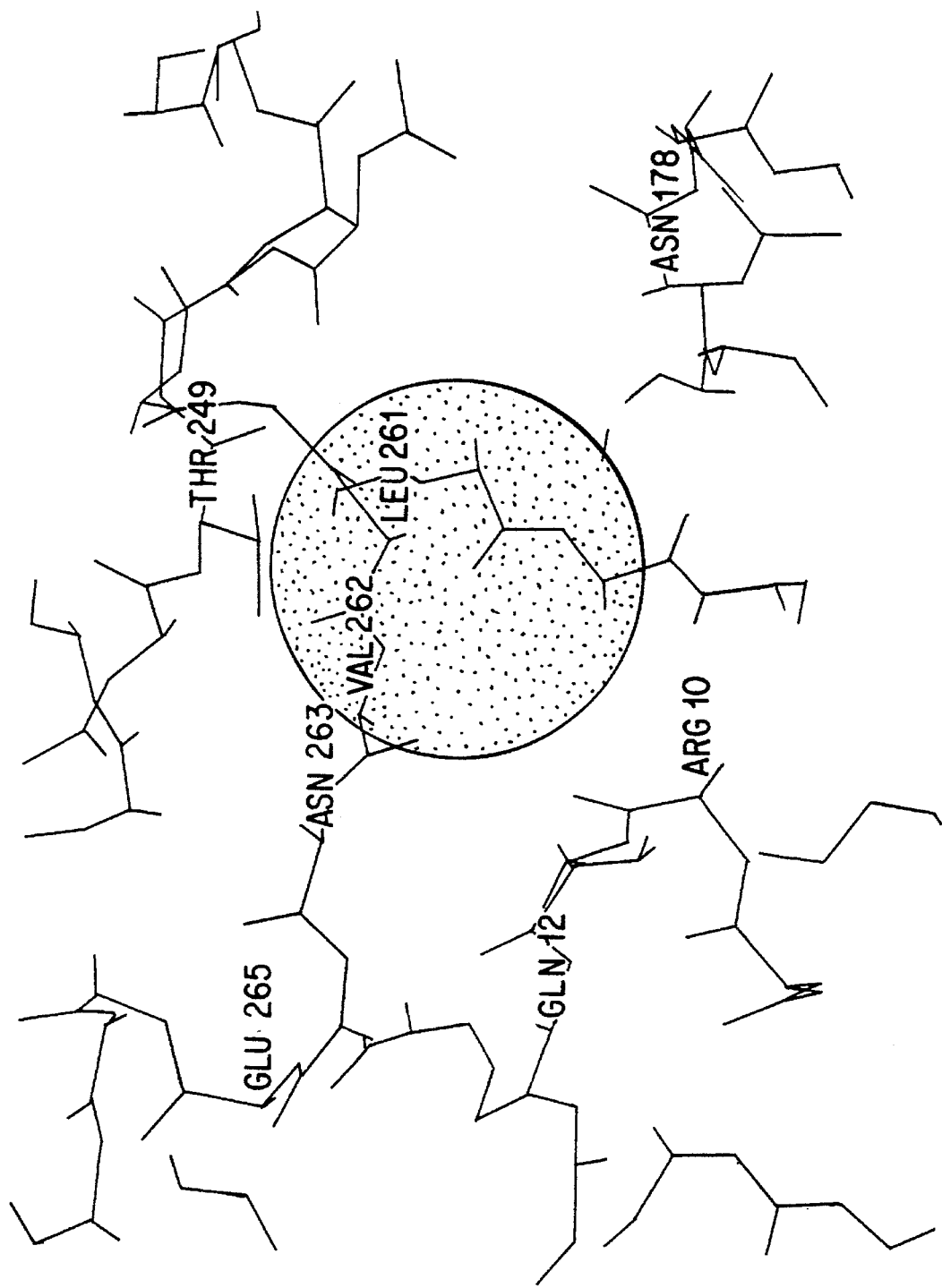
FIG. 11 shows a hydrophobic region at positions Val261–Leu262.
Figure 12:
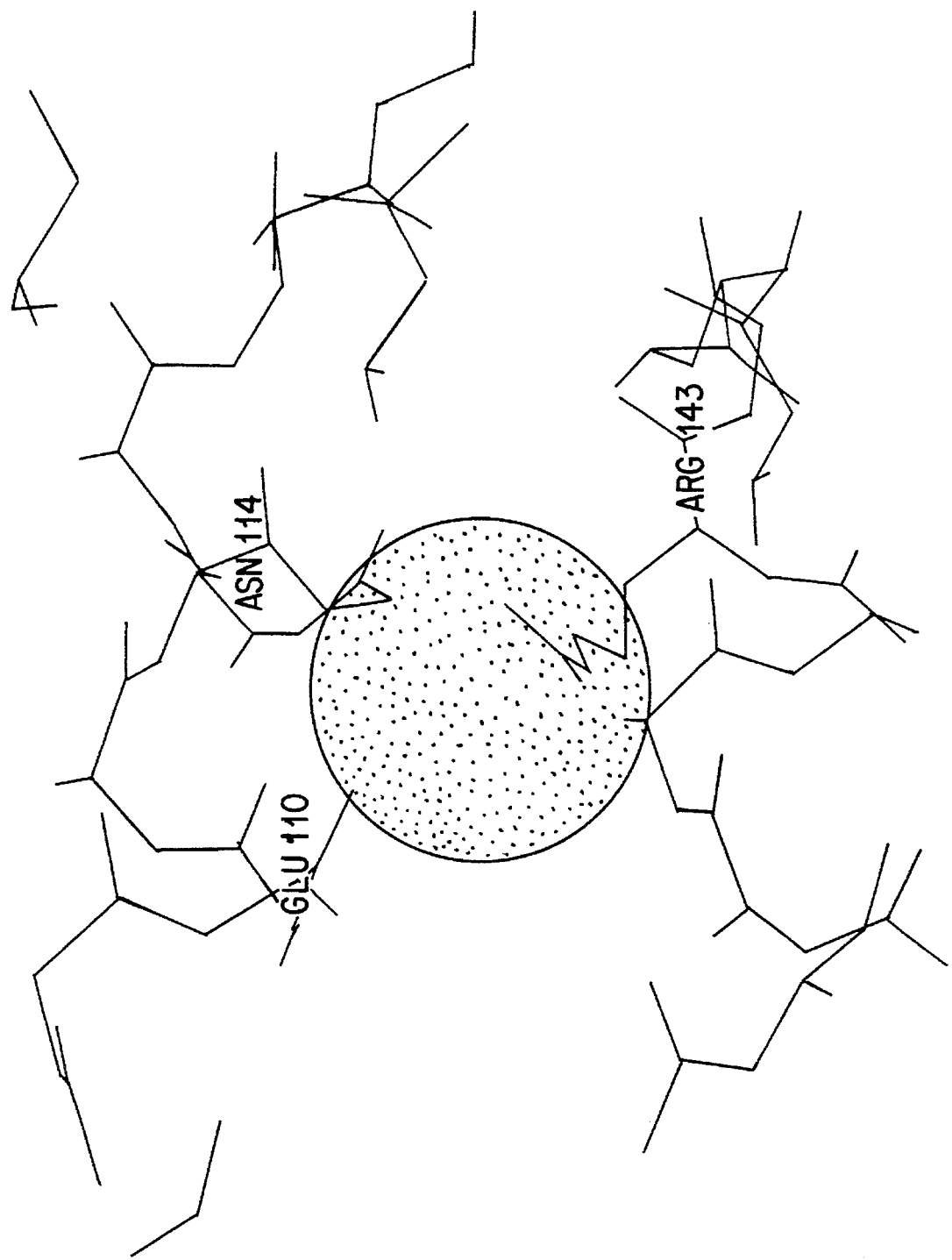
FIG. 12 shows a hydrophobic cavity which penetrates deeply into the interior of the enzyme and in whose vicinity the replaceable ionic amino acid Arg 143 is located.

The construction of the three expression vectors detailed hereinafter was carried out in each case in *E. coli* MC1061. The expression vectors were isolated from ampicillin-resistant *E. coli* transformants. In order to express mutated and non-mutated protease genes, the expression vectors prepared and isolated in this Example were inserted into *B. subtilis* BD224. Selection in this case was for neomycin or phleomycin resistance. The transformants were capable of producing the high-alkaline protease stabilized by mutation (transformants with vectors from sections A. and B. of this Example) or the non-mutated high-alkaline protease (transformants with vector from section C. of this Example). The restriction map of the prepared vectors of the pAL1NC type is depicted in FIG. 8.

A. Expression vector with mutations in the N-terminal part of the DNA sequence of the protease.

The mutated vector pCLMUTN1 obtained by directed mutagenesis as in Example 3 was cut with the restriction endonucleases NcoI and XbaI. The isolated NcoI/XbaI fragment (mutated N-terminal part of the protease structural gene with the mutations K27Q, I43R, I43K, I43Q, I43E, H118W, H118Y) was cloned into the NcoI/XbaI site of the plasmid pAL1C obtained as in Example 10. The resulting vectors represented complete expression vectors with a suitable reading frame for expressing the proteases stabilized by mutation.

B. Expression vector with mutations in the C-terminal part of the DNA sequence of the protease.

The mutated vector pCLMUTC1 obtained by directed mutagenesis as in Example 3 was cut with the restriction endonucleases XbaI and Asp718. The isolated XbaI/Asp718 fragment (mutated C-terminal part of the protease structural gene with the mutations R143N, R143S, R143T, R164Q, N237P, T249R, T249K, T249Q, T249E) was cloned into the XbaI/Asp718 site of the plasmid pAL1N obtained as in Example 10. The resulting vectors represented complete expression vectors with suitable reading frames for expressing the proteases stabilized by mutation.

C. Expression vector with the non-mutated DNA sequence of the initial protease.

The expression vector with the non-mutated initial structural gene of the protease was obtained either by cloning the non-mutated NcoI/XbaI fragment from the plasmid pCLEAN4 obtained as in Example 1 into the NcoI/XbaI site of pAL1C (Example 10); or by cloning the XbaI/Asp718 fragment from the plasmid pCLEAN4 obtained as in Example 1 into the XbaI/Asp718 site of pAL1N (Example 10). The resulting vectors were complete expression vectors with suitable reading frames for expressing the initial protease.

Example 12

Preparation of mutation-stabilized high-alkaline proteases and of unstabilized initial protease for comparison purposes.

50 ml of preculture medium (20 g of tryptone, 10 g of yeast extract, 5 g of NaCl, 75 g of soluble starch, 10 ml of corn steep liquor per liter) were inoculated with one colony of each of the strains to be tested (in each case *B. subtilis* BD224 transformed with one of the pAL1NC vectors prepared in Example 11). Each culture was incubated at 37° C. and 250 rpm for 16 hours. 2.5 ml of each culture were used to inoculate 50 ml of main culture medium (30 g of soya meal, 90 g of potato starch, 10 g of Na caseinate and 10 ml of corn steep liquor per liter). The main cultures were incubated under the same conditions as the precultures. After 72 hours, the cultures were centrifuged. The resulting proteases were precipitated from the culture supernatants with acetone and subsequently purified as follows: Mono S cation exchanger, FPLC; elution with increasing gradient from 20 mM to 200 mM ammonium acetate, pH=6.

On the one hand, the initial protease was obtained, and on the other hand, the stabilized proteases of the amino acid sequence of FIG. 1 (SEQ ID NO:2) with the mutations K27Q, I43K, I43Q, I43E, H118, H118Y, R143N, R143S, R143T, R164Q, N237P, T249R, T249K, T249Q and T249E were obtained.

Example 13

Washing performance of the mutation-stabilized high-alkaline proteases.

The washing performance of proteases stabilized according to the invention were determined by washing tests with various washing agents and for variously soiled fabrics.

13a) The washing performance of the proteases was determined by washing tests on a test fabric EY-PC (egg yolk/ink-stain on polyester-cotton blend fabric—self produced) in laboratory washing machines (Polycolor). For this purpose the test fabric was washed with an aqueous washing solution to which the respective protease being tested had been added in a concentration of 0.71 mg/l. The washing agent (detergent) used was a conventional detergent formulation for a powdered detergent containing customary detergent ingredients [18.4% zeolite, 7.3% $Na_2CO_3$, 4.8% linear alkylbenzenesulfonate, 3.3% non-ionics, 3.3% soap, 0.1% anti-foam agent, 1.5% carboxymethylcellulose, 0.15% optical brightener, 3.8% sodium disilicate, 25% perborate, 1.5% TAED (tetraacetyl ethylenediamine) 30.85% $Na_2SO_4$]. The concentration of the washing agent in the washing solution was 6 g/l. The water used had a water hardness of 15° dH (German hardness scale). Washing was carried out in the temperature range from 15° C. to 60° C. for 45 minutes (2° C./min.; 22.5 min. holding time at 60° C.). The enzyme-containing washing solution was allowed to act on the test fabric in a rotating sample container, the temperature of which was controlled on a water bath in accordance with the test program. After the washing operation, the test fabric was rinsed twice with tap water and subsequently ironed.

The washing performance was determined by measuring the reflectance of the washed test fabric using a remission photometer. For comparison, the reflectance of a test fabric washed under the same conditions but with a washing agent formulation without added protease was likewise determined.

In washing tests using the protease stabilized by a N237P replacement in the amino acid sequence, the measured reflectance of the test fabric was 6.8% higher than with a test fabric washed without added protease.

13b) The washing tests were carried out as described in Example 13a). An enzyme-free detergent formulation as is conventional for a powdered compact complete detergent obtainable from detergent manufacturers was used as the washing agent. The concentration of the washing agent formulation in the washing solution was 3 g/l. In these tests washing was carried out in the temperature range from 15° C. to 40° C. for 45 minutes (2° C./min; 32.5 min. holding time at 40° C.). A polyester-cotton blend fabric (EMPA 117, obtained from the Federal Material Testing Institute, St. Gallen, Switzerland) stained with blood, milk and ink was used as the test fabric.

The washing power of the proteases listed in the following table 1 was investigated. The indicated increase in the reflectance of the washed test fabric is relative to that of a test fabric washed under the same conditions but only with the washing agent formulation without added protease.

TABLE 1

Washing power of proteases stabilized according to the invention on test fabric EMPA 117 in washing tests with a conventional washing agent formulation for a powdered compact complete detergent.

| Protease Stabilized by Amino Acid Replacement in Sequence Position | % Increase in Reflectance of Test Fabric Relative to Test Fabric Washed without Added Protease |
| --- | --- |
| I43Q | 21.3 |
| I43K | 20.9 |
| N114R/N237P | 20.7 |

13c) The washing tests were carried out as described in Example 13b) except that a test fabric EY-PC (egg yolk/ink-stain on polyester-cotton blend fabric—self produced) was used.

The washing power of the proteases listed in the following Table 2 were investigated. As described above, the indicated increase of the reflectance of the test fabric is relative to a test fabric washed under the same conditions but only with the washing agent formulation without added protease.

TABLE 2

Washing power of proteases stabilized according to the invention on test fabric EY-PC in washing tests with a conventional washing agent formulation for a powdered compact complete detergent.

| Protease Stabilized by Amino Acid Replacement in Sequence Position | % Increase in Reflectance of Test Fabric Relative to Test Fabric Washed without Added Protease |
| --- | --- |
| I43Q | 11.0 |
| I43K | 7.7 |

13d) The washing tests were carried out as described in Example 13a. An enzyme-free detergent formulation as is conventional for a liquid complete detergent obtainable from detergent manufacturers was used as the washing agent. The concentration of the washing agent formulation in the washing agent solution was 4 g/l. Washing was carried out in the temperature range from 15° C. to 40° C. for 45 minutes (2° C./min; 32.5 min. holding time at 40° C.). As the test fabric a test fabric EY-PC (egg yolk/ink-stain on polyester-cotton blend fabric—self produced) was used.

The washing performance of the proteases listed in the following Table 3 was investigated. The indicated reflectance of the test fabric is relative to a test fabric washed under the same conditions but only with the washing agent formulation without added protease.

TABLE 3

Washing power of proteases stabilized according to the invention on test fabric EY-PC

TABLE 3-continued in washing tests with a conventional washing agent formulation for a liquid complete detergent.

| Protease Stabilized by Amino Acid Replacement in Sequence Position | % Increase in Reflectance of Test Fabric Relative to Test Fabric Washed without Added Protease |
|---|---|
| T249K | 4.0 |
| T249E | 5.3 |
| I43E | 4.5 |

In all of the washing tests which were carried out a higher reflectance was measured for the test fabrics washed with added protease according to the invention than for a test fabric washed only with the detergent formulation. This shows the very good washing performance of proteases stabilized according to the invention, whereby various protein stains were also removed without any problem from the fabric during the washing operation.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A high-alkaline protease with an amino acid sequence having at least 90% homology to the amino acid sequence of FIG. 1 (SEQ ID NO:2) stabilized against the destabilizing effects of ionic surfactants by at least one of the following amino acid replacements: K27Q, I43R, I43K, I43Q, I43E, Y89Q, H118W, H118Y, R143N, R143S, R143T, R164Q, N237P, T249R, T249K, T249Q and T249E, wherein the position numbers relate to the positions in FIG. 1 (SEQ ID NO:2).

2. A stabilized protease according to claim 1, wherein said protease is a substilisin protease having at least 95% homology to the amino acid sequence of FIG. 1 (SEQ ID NO:2).

3. A detergent composition comprising at least one ionic surfactant and a stabilized protease according to claim 1.

4. A detergent composition according to claim 3, wherein said ionic surfactant is an anionic surfactant.

* * * * *